US009937211B2

(12) United States Patent
Kelly et al.

(10) Patent No.: US 9,937,211 B2
(45) Date of Patent: Apr. 10, 2018

(54) **COMPOSITION OF *ROSEBURIA HOMINIS***

(71) Applicant: 4D Pharma Research Limited, Aberdeen (GB)

(72) Inventors: Denise Kelly, Aberdeen (GB); Imke Mulder, Aberdeen (GB)

(73) Assignee: 4D Pharma Research Limited, Aberdeen (GB)

( * ) Notice: Subject to any disclaimer, the term of this patent is extended or adjusted under 35 U.S.C. 154(b) by 0 days.

(21) Appl. No.: 15/070,605

(22) Filed: Mar. 15, 2016

(65) Prior Publication Data

US 2016/0279177 A1 Sep. 29, 2016

Related U.S. Application Data

(63) Continuation of application No. 14/349,907, filed as application No. PCT/GB2012/052495 on Oct. 8, 2012, now Pat. No. 9,314,489.

(30) Foreign Application Priority Data

Oct. 7, 2011 (GB) .................................. 1117313.5

(51) Int. Cl.

| | | |
|---|---|---|
| *A61K 35/74* | (2015.01) | |
| *A61K 35/741* | (2015.01) | |
| *C12N 1/20* | (2006.01) | |
| *A23K 10/18* | (2016.01) | |
| *A23L 33/135* | (2016.01) | |
| *A61K 9/00* | (2006.01) | |
| *A61K 45/06* | (2006.01) | |
| *A61K 35/00* | (2006.01) | |

(52) U.S. Cl.
CPC ............ *A61K 35/741* (2013.01); *A23K 10/18* (2016.05); *A23L 33/135* (2016.08); *A61K 9/0053* (2013.01); *A61K 35/74* (2013.01); *A61K 45/06* (2013.01); *C12N 1/20* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,816,567 A | 3/1989 | Cabilly et al. | |
| 5,674,707 A | 10/1997 | Hintz et al. | |
| 5,741,665 A | 4/1998 | Kato et al. | |
| 7,749,494 B2 | 7/2010 | Renaud et al. | |
| 7,998,474 B2* | 8/2011 | Kelly | A61K 31/02 424/93.1 |
| 9,314,489 B2* | 4/2016 | Kelly | |
| 9,539,293 B2* | 1/2017 | Kelly | A61K 35/747 |
| 2010/0316617 A1 | 12/2010 | Renaud et al. | |
| 2011/0053829 A1 | 3/2011 | Baumhof et al. | |
| 2015/0071957 A1* | 3/2015 | Kelly | A61K 38/164 424/190.1 |
| 2015/0132264 A1 | 5/2015 | Kelly et al. | |
| 2017/0143772 A1 | 5/2017 | Mulder et al. | |
| 2017/0143773 A1 | 5/2017 | Mulder et al. | |
| 2017/0143774 A1 | 5/2017 | Mulder et al. | |
| 2017/0143775 A1 | 5/2017 | Mulder et al. | |
| 2017/0173089 A1 | 6/2017 | Kelly | |

FOREIGN PATENT DOCUMENTS

| | | |
|---|---|---|
| EP | 0120516 A2 | 10/1984 |
| EP | 0238023 A2 | 9/1987 |
| EP | 0449375 A2 | 10/1991 |
| EP | 2832859 A1 | 2/2015 |
| JP | 2006265212 A | 10/2006 |
| WO | WO-9117243 A1 | 11/1991 |
| WO | WO-9735956 A1 | 10/1997 |
| WO | WO-02085933 A1 | 10/2002 |
| WO | WO-03053220 A2 | 7/2003 |
| WO | WO-2005030133 A2 | 4/2005 |
| WO | WO-2005107381 A2 | 11/2005 |

(Continued)

OTHER PUBLICATIONS

Duncan S. et al Proposal of *Roseburia faecis* sp. nov., *Roseburia hominis* sp. nov. and *Roseburia inulinivorans* sp. nov., Based on Isolates From Human Faeces. Int J Systematic and Evolutionary Microbiology 56:2437-2441, 2006.*
Hoyles L. et al. Gastrointestinal Tract: Intestinal Fatty Acid Metabolism and Implications for Health. Handbook of Hydrocarbon and Lipid Micrbiology 2010, pp. 3120-3129.*
Kingsley M. A Personalized Approach to Managing IBD. Gastroenterology and Hepatology 12(5)308-315, May 2016.*
McIntosh F. et al. Mechanism of Conjugated Linoleic Acid . . . Microbiology 155:285-294, 2009.*
Ukena et al. 'Probiotic *Escherichia coli* Nissle 1917 inhibits leaky gut by enhancing mucosal integrity.' PloS one. 2007, vol. 2, No. 12, pp. e1308.
Untergasser et al. 'Primer3Pius, an enhanced web interface to Primer3.' Nucleic Acids Research. 2007, vol. 35, Suppl. 2, pp. W71-W74.

(Continued)

Primary Examiner — Ralph J Gitomer
(74) Attorney, Agent, or Firm — Wilson Sonsini Goodrich & Rosati

(57) ABSTRACT

A first aspect of the invention relates to the bacterial species *Roseburia hominis* for use in: regulating the immune system of a subject treating an immune disorder; treating an intestinal disorder; improving intestinal microbiota; regulating the innate immune system of a subject; regulating the adaptive immune system of a subject; regulating appetite in a subject; promoting Tregs and immune tolerance; promoting gut health in a subject; and/or maintaining immune homeostasis in a subject. Further aspects of the invention relate to compositions comprising *Roseburia hominis*.

22 Claims, 23 Drawing Sheets

(56) References Cited

FOREIGN PATENT DOCUMENTS

| WO | WO-2007098371 A2 | 8/2007 |
|---|---|---|
| WO | WO-2009030481 A1 | 3/2009 |
| WO | WO-2009079564 A2 | 6/2009 |
| WO | WO-2009128949 A2 | 10/2009 |
| WO | WO-2010037408 A1 | 4/2010 |
| WO | WO-2010037539 A1 | 4/2010 |
| WO | WO-2012142605 A1 | 10/2012 |
| WO | WO-2013050792 A1 | 4/2013 |
| WO | WO-2014167338 A1 | 10/2014 |
| WO | WO-2016102951 A1 | 6/2016 |

OTHER PUBLICATIONS

Vijay-Kumar et al. 'Deletion of TLR5 results in spontaneous colitis in mice.' The Journal of Clinical Investigation. 2007, vol. 117, No. 2, pp. 3909-3921.

Werth et al. 'The transcription factor grainyhead-like 2 regulates the molecular composition of the epithelial apical functional complex.'. Development. 2010, vol. 137, No. 22, pp. 3835-3845.

McIntosh et al. 'Mechanism of conjugated linoleic acid and vaccenic acid formation in human faecal suspensions and pure cultures of intestinal bacteria.' Microbiology. 2009, vol. 155, No. 1, pp. 285-294.

Falony et al. 'In vitro kinetics of prebiotic inulin-type fructan fermentation by butyrate-producing colon bacteria: implementation of online gas chromatography for quantitative analysis of carbon dioxide and hydrogen gas production.' Applied and Environmental Microbiology. 2009, vol. 75, No. 18, pp. 5884-5892.

Nieyrinck et al. 'Dietary modulation of clostridial cluster XIVa gut bacteria (*Roseburia* spp.) by chitin-glucan fiber improves host metabolic alterations induced by high-fat diet in mice.' The Journal of Nutritional Biochemistry. 2012, vol. 23, No. 1, pp. 51-59.

Overstreet et al. 'Dysbiosis Characterized by Reduced Abundance of Roseburia is Associated With Increased Severity of Colitis in IL-10-/- Mice'. Gastroenterology. 2011, vol. 140, No. 5, Suppl. 1, pp. S-696.

Pryde et al. 'The microbiology of butyrate formation in the human colon.' FEMS Microbiology Letters. 2002. vol. 217, No. 2, pp. 133-139.

International Search Report for Internation Application No. PCT/GB2012/052495, dated Mar. 3, 2013 (4 pages).

International Search Report for PCT Application No. PCT/GB2012/052495. dated Mar. 11, 2013. 4 pages.

Duncan. Sylvia H. et al. '*Rosebura intestinalis* sp. nov., A Novel Saccharolytics, Butyrate-producing Bacterium from Human Feces'. International Journal of Systematic and Evolutionary Microbiology. 2002, vol. 52, pp. 1615-1620.

Duncan, Sylvia H. et al. 'Proposal of *Roseburia faecis* sp. nov., *Roseburia hom* in is sp. nov. and *Roseburia inulinivorans* sp. nov., Based on Isolates from Human Feces'. International Journal of Systematic and Evolutionary Microbiology. 2006, vol. 56, pp. 2437-2441.

Hoyles L. et al. Gastrointestinal Tract, Chapter 56. Handbook of Hydrocarbon and Lipid Microbiology Springer Verlag Berlin 2010, 3120-32.

Tilg, H. et al. Roseburia hominis. Gut 63(8)1204-1205, Oct. 14, 2013.

Reiff C. et al. IBD, Gut Bacteria and Probiotic Therapy. Int J Medical Microbiology 300:25-33, 2010.

Lakhdari, et al. Identification of NF-κB Modulation Capabilities within Human Intestinal Commensal Bacteria. J Biomed Biotechnol. 2011; 2011: 282356.

Notice allowance dated Feb. 3, 2016 for U.S. Appl. No. 14/349,907.

Office action dated Jul. 8, 2015 for U.S. Appl. No. 14/349,907.

Extended European search report and opinion dated Aug. 23, 2016 for EP Application No. 16166001.4.

Travis, et al. Complete genome sequence of the human gut symbiont Roseburia hominis. Genome announcements. 2015; 3(6):e01286-15.

Barcenilla et al. "Phylogenetic relationships of butyrate-producing bacteria from the human gut" Applied and environmental microbiology. 2000, vol. 66, No. 4, pp. 1654-1661.

Duncan et al. "Lactate-utilizing bacteria, isolated from human feces, that produce butyrate as a major fermentation product" Applied and environmental microbiology. 2004, vol. 70, No. 10, pp. 5810-5817.

Hold et al. 'Oligonucleotide probes that detect quantitatively significant groups of butyrate-producing bacteria in human feces.' Applied and environmental microbiology. 2003, vol. 69, No. 7, pp. 4320-4324.

Louis et al. 'Diversity, metabolism and microbial ecology of butyrate—producing bacteria from the human large intestine.' FEMS Microbiology Letters. 2009, vol. 294, No. 1, pp. 1-8.

Louis et al. 'Diversity of human colonic butyrate—producing bacteria revealed by analysis of the butyryl—GoA: acetate GoA—transferase gene.' Environmental Microbiology. 2010, vol. 12, No. 2, pp. 304-314.

Rusell et al. 'High-protein, reduced-carbohydrate weight-loss diets promote metabolite profiles likely to be detrimental to colonic health.' The American Journal of Clinical Nutrition. 2011, vol. 93, No. 5, pp. 1062-1072.

Scott et al. 'Substrate-driven gene expression in Roseburia inulinivorans: importance of inducible enzymes in the utilization of inulin and starch.' Proceedings of the National Academy of Sciences. 2011, vol. 108, Supp. 1, pp. 4672-4679.

Sokol et al. 'Low counts of Faecalibacterium prausnitzii in colitis microbiota.' Inftammatory bowel diseases. 2009, vol. 15, No. 8, pp. 1183-1189.

Van Immerseel et al. 'Butyric acid-producing anaerobic bacteria as a novel probiotic treatment approach for inflammatory bowel disease.' Journal of medical microbiology. 2010, vol. 59, No. 2, pp. 141-143.

Walker et al. 'Dominant and diet-responsive groups of bacteria within the human colonic microbiota.' The ISME Journal. 2010, vol. 5, No. 2, pp. 220-230.

Altschul et al. 'Basic local alignment search tool.' Journal of Molecular Biology. 1990, vol. 215, No. 3, pp. 403-410.

Ami Nov et al. 'Molecular diversity, cultivation, and improved detection by fluorescent in situ hybridization of a dominant group of human gut bacteria related to *Roseburia* spp. or Eubacterium rectale.' Applied and environmental microbiology. 2006, vol. 72, No. 9, pp. 6371-6378.

Aziz et al. 'The RAST Server rapid annotations using subsystems technology.' BMC Genomics. 2008, vol. 9, No. 1, pp. 75.

Chevreux et al. 'Genome sequence assembly using trace signals and additional sequence information.' German Conference on Bioinformatics. 1999.

Chung et al. 'Microbiota-stimulated immune mechanisms to maintain gut homeostasis.' Current Opinion in Immunology. 2010, vol. 22, No. 4, pp. 455-460.

De Paepe et al. 'Trade-off between bile resistance and nutritional competence drives *Escherichia coli* diversification in the mouse gut.' PLoS Genetics. 2011, vol. 7, No. 6, e1002107.

Dennis et al. 'DAVID: database for annotation, visualization, and integrated discovery.' Genome Bioi. 2003, vol. 4, No. 5, pp. 3.

Duck et al. 'Isolation of flagellated bacteria implicated in Crohn's disease.' Inflammatory Bowel Diseases. 2007, vol. 13, No. 10, pp. 1191-1201.

Duncan et al. 'Proposal of *Roseburia faecis* sp. nov., *Roseburia hominis* sp. nov. and *Roseburia inulinivorans* sp. nov., based on isolates from human faeces.' International journal of systematic and evolutionary microbiology. 2006, vol. 56, No. 10, pp. 2437-2441.

Eckburg et al. 'Diversity of the human intestinal microbial flora.' Science. 2005, vol. 308, No. 5728, pp. 1635-1638.

Elkins et al. 'Genes encoding bile salt hydrolases and conjugated bile salt transporters in Lactobacillus johnsonii 100-100 and other *Lactobacillus* species.' Microbiology. 2001, vol. 147, No. 12, pp. 3403-3412.

Gaboriau-Routhiau et al. 'The key role of segmented filamentous bacteria in the coordinated maturation of gut helper T cell responses.' Immunity. 2009, vol. 31, No. 4, pp. 677-689.

(56) References Cited

OTHER PUBLICATIONS

Geraedts et al. 'Release of satiety hormones in response to specific dietary proteins is different between human and murine small intestinal mucosa.' Annals of Nutrition and Metabolism. 2010, vol. 56, No. 4, pp. 3018-313.
Geuking et al. 'Intestinal bacterial colonization induces mutualistic regulatory T cell responses.' Immunity. 2011, vol. 34, No. 5, pp. 794-806.
Giraud et al. 'Dissecting the genetic components of adaptation of *Escherichia coli* to the mouse gut.' PLoS Genetics. 2008, vol. 4, No. 1, pp. e2.
Hapfelmeier et al. 'Reversible microbial colonization of germ-free mice reveals the dynamics of IgA immune responses.' Science. 2010, vol. 328, No. 5986, pp. 1705-1709.
Hayashi et al. The innate immune response to bacterial flagellin is mediated by Toll-like receptor 5. Nature. 2001, vol. 410, No. 6832, pp. 1099-1103.
Hooper at al. 'Molecular analysis of commensal host-microbial relationships in the intestine.' Science. vol. 291, No. 5505, pp. 881-884.
Ivanovetal. 'Induction of intestinal Th17 cells by segmented filamentous bacteria.' Cell. 2009, vol. 139, No. 3, pp. 485-489.
Kelly et al. 'Commensal anaerobic gut bacteria attenuate inflammation by regulating nuclear-cytoplasmic shuttling of PPAR-y and RelA.' Nature Immunology. 2003, vol. 5, No. 1, pp. 104-112.
Letran et al. 'TLR5-deticient mice lack basal inflammatory and metabolic defects but exhibit impaired CD4 T cell D responses to a flagellated pathogen.' The Journal of Immunology. 2011, vol. 186, No. 9, pp. 5406-5412.
Louis et al. 'Organization of butyrate synthetic genes in human colonic bacteria: phylogenetic conservation and horizontal gene transfer.' FEMS Microbiology Letters. 2007, vol. 269, No. 2, pp. 240-247.
MacPherson et al. 'IgA responses in the intestinal mucosa against pathogenic and non-pathogenic microorganisms.' Microbes and Infection. 2001, vol. 3, No. 12, pp. 1021-1035.
MacPherson et al. The functions of mucosal T cells in containing the indigenous commensal flora of the intestine. Cellular and Molecular Life Sciences CMLS. 2002, vol. 59, No. 12, pp. 2088-2096.
MacPherson et al. 'IgA adaptation to the presence of commensal bacteria in the intestine.' Gut-Associated Lymphoid Tissues. Springer Berlin Heidelberg, 2006. 117-136.
Mahowald et al. 'Characterizing a model human gut microbiota composed of members of its two dominant bacterial phyla.' Proceedings of the National Academy of Sciences. 2009, vol. 106, No. 14, pp. 5859-5864.
Mallya et al. 'Characterization of the five novel Ly-6 superfamily members encoded in the MHC, and detection of cells expressing their potential ligands.' Protein Science. 2006, vol. 15, No. 10, pp. 2244-2256.
Mazmanian et al. 'An immunomodulatory molecule of symbiotic bacteria directs maturation of the host immune system.' Cell. 2005, vol. 122, No. 1, pp. 107-118.
McLaughlin et al. Fatty acid chain length determines cholecystokinin secretion and effect on human gastric motility. Gastroenterology. 1999, vol. 116, No. 1, pp. 46-53.
Olivera et al. 'Nutritional and physiological responses of young growing rats to diets containing raw cowpea seed meal, protein isolate (globulins), or starch.' Journal of agricultural and food chemistry. 2003, vol. 51, No. 1, pp. 319-32c.
Peterson et al. 'Catecholamines increase conjugative gene transfer between enteric bacteria.' Microbial Pathogensis. 2011, vol. 51, No. 1, pp. 1-8.
Qin et al. 'A human gut microbial gene catalogue established by metagenomic sequencing.' Nature. 2010, vol. 464, No. 7285, pp. 59-65.
Round et al. 'The Toll-like receptor 2 pathway establishes colonization by a commensal of the human microbiota.' Science. 2011, vol. 332, No. 6032, pp. 974-977.
Salminen et al. 'Probiotics: how should they be defined?.' Trends in Food Science & Technology. 1999, vol. 10, No. 3, pp. 107-110.
Sokol et al. 'Faecalibacterium prausnitzii is an anti-inflammatory commensal bacterium identified by gut microbiota analysis of Crohn disease patients.' Proceedings of the National Academy of Sciences. 2008, vol. 105, No. 43, pp. 16731-16736.
Spor et al. 'Unravelling the effects of the environment and host genotype on the gut microbiome.' Nature Reviews Microbiology. 2011, vol. 9, No. 4, pp. 279-290.
Tatusova et al. 'BLAST 2 Sequences, a new tool for comparing protein and nucleotide sequences.' FEMS Microbiology Letters. 1999, vol. 174, No. 2, pp. 247-250.
Tremaroli et al. 'A role for the gut microbiota in energy harvesting?.' Gut. 2010.
Turnbaugh et al. 'Diet-induced obesity is linked to marked but reversible alterations in the mouse distal gut microbiome.' Gel Host & Microbe. 2008, vol. 3, No. 4, pp. 213-223.
Turnbaugh et al. 'An obesity-associated gut microbiome with increased capacity for energy harvest.' Nature. 2006, vol. 444, No. 7122, pp. 1027-1031.
An et al. (1985) "New cloning vehicles for transformation of higher plants," EMBO J. 4:277-284.
An et al. (1986) "Transformation of Tobacco, Tomato, Potato, and *Arabiodopsis thaliana* Using a Binary Ti Vector System," Plant Physiol. 81:301-305.
An et al. (1988) "Binary Vectors," Plant Molecular Biology Manual. A3:1-19.
Archer et al. (1997) "The Molecular Biology of Secreted Enzyme Production by Fungi," Critical Reviews Biotechnology. 17(4):273-306.
Atarashi et al. Induction of colonic regulatory T cells by indigenous *clostridium* species. Science 331(6015):337-341 (2011).
Ausubel et al. (1999) Short Protocols in Molecular Biology. 4th edition. pp. 7-58 to 7-60, and Chapter 18. pp. 18-1 to 18-23.
Beggs (1978) "Transformation of yeast by a replicating hybrid plasmid," Nature. 275:104-109.
Berg et al. (1996) "Enterocolitis and colon cancer in interleukin-10-deficient mice are associated with aberrant cytokine production and CD4(+) TH1-like responses," the Journal of Clinical Investigation. 98(4):1010-1020.
Brasel et al. (2000) "Generation of murine dendritic cells from flt3-ligand-supplemented bone marrow cultures," Blood. 96(9):3029-3039.
Butcher et al. (1980) Tissue Culture Methods for Plant Pathologists. Eds.: Ingrams, D. S.; Helgeson, J.P. pp. 203-208.
Carvalho et al. (Jan. 2011) "TLR5 activation induces secretory interleukin-1 receptor antagonist (sll-1 Ra) and reduces inftammasome-associated tissue damage," Nature. 4(1 ):102-111.
Cereghino et al. (2000) "Heterologous protein expression in the methylotrophic yeast *Pichia pastoris*," FEMS Microbiol Review. 24(1 ):45-66.
Chothia et al. The relation between the divergence of sequence and structure in proteins. EMBO Journal. 1986, 5(4):823-826.
Christou (1994) "Genetic engineering of crop legumes and cereals: current status and recent advances," Agro-Food Industry Hi-Tech. pp. 17-27.
Co-pending U.S. Appl. No. 15/359,144, filed Nov. 22, 2016.
Co-pending U.S. Appl. No. 15/592,178, filed May 10, 2017.
Co-pending U.S. Appl. No. 15/631,945, filed Jun. 23, 2017.
Co-pending U.S. Appl. No. 15/631,952, filed Jun. 23, 2017.
Co-pending U.S. Appl. No. 15/673,270, filed Aug. 9, 2017.
Co-pending U.S. Appl. No. 15/679,857, filed Aug. 17, 2017.
Crellin et al. (2005) "Human CD4+ T cells express TLR5 and its ligand ftagellin enhances the suppressive capacity and expression of FOXP3 in CD4+CD25+ T regulatory cells," Journal of Immunology. 175(12):8051-8059.
Davis et al., Genetic and Microbiological Research Techniques, Methods Enzymol. 1970; 17A:79-143.
Ely et al. (2000) "A family of six flagellin genes contributes to the Caulobacter crescentus flagellar filament," Journal of Bacteriology. 182(17):5001-5004.

(56) References Cited

OTHER PUBLICATIONS

FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.
Flores-Langarica et al. (2012) "Systemic flagellin immunization stimulates mucosal CD1 03+ dendritic cells and drives Foxp3+ regulatory T Cell and IgA responses in the mesenteric lymph node," Journal of Immunology. 189 ( 12):57 45/5754.
Fraley et al. (1986) "Genetic Transformation in Higher Plants," Critical Reviews Plant Science. 4:1-46.
Frame et al. (1994) "Production of fertile transgenic maize plants by silicon carbide whisker-mediated transformation," the Plant Journal. 6:941-948.
Frank, D. et al., Molecular-phylogenetic characterization of microbial community imbalances in human inflammatory bowel diseases. 2007. PNAS. 104(34):13780-5.
Gait, M.J., (1984) Oligonucleotide Synthesis: A Practical Approach. Irl Press. pp. vii-xiii.
GB Search and Exam report dated Apr. 20, 2016 for GB application 1510468.0.
GenBank Accession No. ABI48297.1 (Jul. 20, 2007) "Fia1 flagellin [*Roseburia hominis*]".
GenBank Accession No. ABY J02000000 (Nov. 8, 2013) Version 2. "Roseburia intestinal is L 1-82, whole genome shotgun sequencing project".
GenBank Accession No.'s ABY J02000001—ABY J02000409 search results page (Last Updated Apr. 24, 2015).
GenBank accession No. AJ312385 (Oct. 9, 2002) "Roseburia intestinalis 16S rRNA gene, strain L 1-82".
GenBank Accession No. CP003040 (Aug. 5, 2011) Version 1. "Roseburia Hominis A2-183, complete genome".
GenBank Accession No. DQ789141. (Jul. 20, 2007) "Roseburia horn in is Fla2 flagellin gene".
GenBank Accession No. M20983. (Apr. 26, 1993) "R.cecicola ftagellin gene".
Gennaro, A.R., Remington's Pharmaceutical sciences, Mack publishing co. 1985.
Gewirtz et al. (2001) Cutting edge: bacterial flagellin activates basolaterally expressed TLR5 to induce epithelial proinflammatory gene expression. The Journal of Immunology. 167:(4)1882-1885.
Greenspan et al., Defining epitopes: It's not as easy as it seems. Nature Biotechnology 7: 936-937, 1999.
Hedayat et al. (Mar. 1, 2012) "Prophylactic and therapeutic implications of toll-like receptor ligands," Medicinal Research Reviews. 32(2):294-325.
Higgins et al. (1988) "CLUSTAL: a package for performing multiple sequence alighment on a microcomputer," Gene. 73(1 ): 237 -244.
Hinchliffe (1993) "Yeast as a vehicle for the expression of heterologous genes," Yeasts. 2nd edition. Rose, A. R.; Harrison, J. H.: Eds. Academic Press Ltd. 5(9). pp. 325-356.
Hinnen et al. (1978) "Transformation of yeast," Proc. Natl. Acad. Sci. USA. 75:1929-1933.
Hoekema (1985) The Binary Plant Vector System Offset-drukkerij Kanters BB, Alblasserdam. Chapter V. pp. 63-71.
Holland et al. (1990) "Secretion of Heterologous Proteins in *Escherichia coli*," Methods Enzymology. 182:132-143.
Hollenberg et al. (1997) "Production of recombinant proteins by methulotrophic yeasts," Current Opinion Biotechnology. 8(5):554-560.
Hossain et al. "Flagellin, a TLR5 agonist, reduces graft-versus-host disease in allogeneic hematopoietic stem cell transplantation recipients while enhancing antiviral immunity," Journal of Immunology. Nov. 2011; 187(10): p. 5130-5140.
Ibrahim et al. (1985) "Method for the isolation of highly purified *Salmonella flagellins*," Journal of Clinical Microbiology. 22(6):1040-1044.

Inaba et al. (1992) "Generation of large numbers of dendritic cells from mouse bone marrow cultures supplemented with granulocyte/ macrophage colony-stimulating factor," J. Exp. Med. 176(6):1693-1702.
International Preliminary Report on Patentability corresponding to International Patent Application No. PCT/GB2014/051123, dated Oct. 13, 2015.
International Search Report dated Aug. 21, 2014 for International Application No. PCT/GB2014/051123.
International Search Report dated Aug. 26, 2016 for International application No. PCT/GB2016/051774.
Ito et al. (1983) "Transformation of Intact Yeast Cells Treated with Alkali Cations," J. Bacteriology. 153:163-168.
Jarchum et al. (Jan. 2011) "Toll-Like Receptor 5 Stimulation Protects Mice from Acute Clostridium difficile Colitis," Infection and Immunity. 79(4):1498-1503.
Kang et al. (201 0) "Dysbiosis of fecal microbiota in Crohn's disease patients as revealed by a custom phylogenetic microarray," Inflammatory Bowel Diseases. 16(12):2034-2042.
Kinnebrew et al. (Feb. 2012) Interleukin 23 production by intestinal CD1 03(+)CD11 b(+) dendritic cells in response to Interleukin 23 production by intestinal CD1 03(+ )CD11 b(+) dendritic cells in response to bacterial flagellin enhances.
Lavallie et al. (1995) "Gene fusion expression systems in *Escherichia coli*," Current Opinion Biotechnology. 6 (5):501-506.
Lilley et al. (1992) Methods in Enzymology; DNA Structure Part A: Synthesis and Physical Analysis of DNA. vol. 2011. pp. v-vii.
Machiels et al. (Feb. 14-16, 2013) "Predominant dysbiosis in patients with ulcerative colitis is different from Crohn's disease patients," Inflammatory Bowel Diseases. 8th Congress of ECCO. (This Abstract is in 7th Congress 2012).
Machiels, K. A decrease of the butyrate-producing species Roseburia hominis and Faecalibacterium prausnitzii defines dysbiosis in patients with ulcerative colitis.Gut. Aug. 2014;63(8):1275-83. doi: 10.1136/gutjnl-2013-304833. Epub Sep. 10, 2013.
Martin et al. (1988) "Cloning, Nucleotide Sequence, and Taxonomic Implications of the Flagellin Gene of Roseburia cecicola," Journal of Bacteriology. 170(6):2612-2617.
Meyer et al. (1992) "The use of cassava mosaic virus as a vector system for plants," Gene. 110:213-217.
Mikayama, et al., Molecular cloning and functional expression of a cDNA encoding glycosylation-inhibiting factor. Proc.Nati.Acad. Sci. USA, Nov. 1993; vol. 90: 10056-1 0060.
Monteleone et al. (2008) "IL-10-dependent partial refractoriness to Toll-like receptor stimulation modulates gut mucosal dendritic cell function," European Journal of Immunology. 38(6):1533-1547.
Neish et al. (2006) "TLR5 in the Gut. II. Flagellin-induced inflammation and antiapoptosis," American Journal of Physiology-Gastrointestinal and Liver Physiology. 292:G462-466.
Neville et al. (Jul. 10, 2012) "Characterization of pro-inflammatory flagellin proteins produced by Lactobacillus ruminis and related motile Lactobacilli," PloS one. 7(7):e40592.
Neville (Jan. 15, 2013) "Functional genomics of motile commensal intestinal bacteria" PhD Thesis. University College Cork. 15 Cork, Republic of Ireland. p. 87. paragraph 1.2.2.4.
Ng et al. (2006) "Archaeal flagella, bacterial flagella and type IV pili: a comparison of genes and posttranslation modification," Journal of Molecular Microbiology and Biotechnology. 11:167-191.
Notice of Allowance dated Mar. 6, 2017 for U.S. Appl. No. 14/249,710.
Notice of allowance dated Jun. 16, 2017 for U.S. Appl. No. 14/249,710.
Notice of allowance dated Sep. 6, 2017 for U.S. Appl. No. 14/249,710.
Notice of Allowance dated Nov. 17, 2016 for U.S. Appl. No. 14/249,710.
Nutsch et al. (2012) "T cell tolerance and immunity to commensal bacteria," Current Opinion in Immunology. 24 (4):385-391.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.

(56) References Cited

OTHER PUBLICATIONS

Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 6, 2006 for U.S. Appl. No. 10/285,224.
Office Action dated Nov. 23, 2015 for U.S. Appl. No. 14/232,475.
Office Action dated Dec. 13, 2012 for U.S. Appl. No. 12/760,926.
Office Action dated Dec. 19, 2005 for U.S. Appl. No. 10/275,706.
Polak et al. (1990) In Situ Hybridization: Principles and Practice, Oxford University Press. pp. vii-viii.
Potrykus (1991) "Gene Transfer to Plants: Assessment of Published Approaches and Results," Annu. Rev. Plant Physiol. Plant Mol. Biol. 42:205-225.
Prakash et al. (Sep. 15, 2011) "Complete genome sequences of rat and mouse segmented filamentous bacteria, a potent inducer ofth17 cell differentiation," Cell Host & Microbe. 10(3):273-284.
Punt et al. (2002) "Filamentous fungi as cell factories for heterologous protein production," Trends Biotechnol. 20 (5):200-206.
Rhee et al. (2008) "Toll-Like Receptor 5 Engagement Modulates Tumor Development and Growth in a Mouse Xenograft Model of Human Colon Cancer," Gastroenterology. 135(2):518-528.
Roe et al. (1996) DNA Isolation and Sequencing: Essential Techniques. John Wiley & Sons, New York, New York. pp. v-vii.
Rudinger et al., Characteristics of the amino acids as components of a peptide hormone sequence. Peptide Hormones. Biol. Council. Jun. 1976; pp. 5-7.
Salonen et al., Gastrointestinal microbia in irritable bowel syndrome: present state and perspectives. Microbiology. 2010; 156: 3205-3215.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Schulke et al. (Aug. 26, 2011) "A fusion protein of flagellin and ovalbumin suppresses the 25 TH2 response and prevents murine intestinal allergy," the Journal of Allergy and Clinical Immunology. 128(6):1340-1348.
Sczesnak et al. (Sep. 15, 2011) "The genome of th17 cell-inducing segmented filamentous bacteria reveals extensive auxotrophy and adaptations to the intestinal environment," Cell Host & Microbe. 10 (3):260-272.
Shevach et al. (1992) Current Protocols in Immunology. John Wiley & Sons. New York, New York. Table of Contents only, as accessed online at URL: http://www.4ulr.com/products/currentprotocols/immunology_toc.html. [Last Accessed Jun. 18, 2015].
Skountzou et al. (2010) "*Salmonella flagellins* are potent adjuvants for intranasally administered whole inactivated influenza vaccine," Vaccine. 28(24):4103-4112.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.
Tatusova et al. (1999) "Erratum to 'BLAST 2 Sequences, a new tool for comparing protein and nucleotide sequences' [FEMS Microbial. 174 (1999) 247-250]," FEMS Microbial. Lett. 177(1):187-188.
Trueman (1995) "Heterologous Expression in Yeast," Methods Molecular Biology. 49:341-354.
Turner (1994) "Vectors for genetic manipulation," In; Martinelli, S.D.; Kinghorn J. R.: Eds. Aspergillus: 50 years on. Progress in industrial microbiology. vol. 29. Elsevier. Amsterdam, the Netherlands. pp. 641-666.
Vijay-Kumar et al. (2008) "Fiagellin Treatment Protects against Chemicals, Bacteria, Viruses, and Radiation," the Journal of Immunology. 180(12):8280-8285.
Watson et al. (2005) "Signal transduction in Campylobacter jejuni-induced cytokine production," Cellular Microbiology. 7(5):655-665.
Weigel et al. (2002) "Comparative analysis of murine marrow-derived dendritic cells generated by Flt3L or GMCSF/IL-4 and matured with immune stimulatory agents on the in vivo induction of antileukemia responses," Blood. 100 (12):4169-4176.
Wilson et al. (Nov. 2012) "The Toll-like receptor 5ligand flagellin promotes asthma by priming allergic responses to indoor allergens," Nature Medicine. 18(11):1705-1710.
Xu et al. (2007) "Differential development of murine dendritic cells by GM-CSF versus Flt3 ligand has implications for inflammation and trafficking," J. Immunol. 179(11):7577-7584.
Yoon et al. (Feb. 2012) "Structural basis ofTLR5-flagellin recognition and signaling," Science. 335(6070):859-864.
Co-pending U.S. Appl. No. 15/700,007, filed Sep. 8, 2017.
Co-pending U.S. Appl. No. 15/704,245, filed Sep. 14, 2017.

\* cited by examiner

COMPOSITION OF *ROSEBURIA HOMINIS*

CROSS REFERENCE

This application is a continuation of U.S. application Ser. No. 14/349,907, filed Apr. 4, 2014, which is a 371 of International Application No. PCT/GB2012/052495 filed Oct. 8, 2012, which claims priority to UK Application No. 1117313.5, filed Oct. 7, 2011 all of which are herein incorporated by reference in their entirety.

SEQUENCE LISTING

The instant application contains a Sequence Listing which has been submitted in ASCII format via EFS-Web in U.S. application Ser. No. 14/349,907 and is hereby incorporated by reference in its entirety. Said ASCII copy, is named "556332_DYT08US_SL" and is 1,123 bytes in size.

BACKGROUND TO THE INVENTION

The present invention relates to the bacterial species *Roseburia hominis* and various nutritional and therapeutic uses thereof.

The human intestine, thought to be initially sterile in utero, is exposed to a large variety of maternal and environmental microbes immediately after birth. The subsequent colonization and succession events in the gut remain dynamic during the first years of life, after which the microbiota becomes adult-like and relatively stable (1). The human gut microbiota contains more than 500 different phylotypes belonging essentially to two major bacterial divisions, the Bacteroidetes and the Firmicutes (2). The successful symbiotic relationships arising from bacterial colonization of the human gut have yielded a wide variety of metabolic, structural, protective and other beneficiary functions. The enhanced metabolic activities of the colonized gut ensure that dietary components, which are otherwise indigestible, are degraded with released byproducts providing an important nutrient source for the host. Similarly, the immunological importance of the gut microbiota is well-recognized and exemplified in germfree animals which have an impaired immune system that is functionally reconstituted following the introduction of commensal bacteria (3-5).

In sharp contrast to the production of secretory intestinal IgA which is influenced by microbial colonization per se (6, 7), T cell development and differentiation seems to require colonization of specific commensal micro-organisms. *Clostridium* species, in particular the spore-forming segmented filamentous bacteria (SFB), appear to be a major driver for the maturation of intestinal Th1, Th17 and Tregs (8, 9). Recent studies have, however, now shown that other gut bacteria including those of the altered Schaedler flora can induce de novo generation of Tregs while mono-colonization with *Bacteroides fragilis* can correct the Th1/Th2 imbalance in germfree mice by promoting the expansion of Tregs (5, 10).

The present invention seeks to elucidate other resident gut bacteria that can modulate metabolic activity in the gut and/or play a role in immunoregulatory processes.

STATEMENT OF INVENTION

The present invention centres on the activity of the bacterial species *Roseburia hominis*, a member of the Firmicutes phylum. Studies by the applicant have demonstrated that this bacterial species plays an important part in immunoregulation and metabolic activity in the gut, as well as having an effect on appetite and satiety genes. The roles of bacterial genes participating in colonization and adaptation to the murine gut, as well as the host genes responding to colonization by this bacterium are described in more detail below.

Aspects of the invention, together with preferred embodiments, are set forth in the accompanying claims.

A first aspect of the invention relates to the bacterial species *Roseburia hominis* for use in regulating the immune system of a subject.

Another aspect of the invention relates to the bacterial species *Roseburia hominis* for use in treating a disorder selected from an inflammatory disorder, an immune disorder and an intestinal disorder.

Another aspect of the invention relates to the bacterial species *Roseburia hominis* for use in promoting gut health by restoring immune homeostasis.

Another aspect of the invention relates to the bacterial species *Roseburia hominis* for use in improving intestinal microbiota in a subject.

Another aspect of the invention relates to the bacterial species *Roseburia hominis* for use in regulating the innate immune system of a subject.

Another aspect of the invention relates to the bacterial species *Roseburia hominis* for use in regulating the adaptive immune system of a subject.

Another aspect of the invention relates to the bacterial species *Roseburia hominis* for use in promoting Tregs and immune tolerance of a subject.

Another aspect of the invention relates to the bacterial species *Roseburia hominis* for use in regulating appetite in a subject.

Another aspect of the invention relates to the use of the bacterial species *Roseburia hominis* in the preparation of a medicament for regulating the immune system of a subject.

Another aspect of the invention relates to the use of the bacterial species *Roseburia hominis* in the preparation of a nutritional supplement or medicament for treating a disorder selected from an inflammatory disorder, an immune disorder and an intestinal disorder in a subject.

Another aspect of the invention relates to the use of the bacterial species *Roseburia hominis* in the preparation of a nutritional supplement or medicament for improving intestinal microbiota in a subject.

Another aspect of the invention relates to the use of the bacterial species *Roseburia hominis* in the preparation of a nutritional supplement or medicament for regulating the innate immune system of a subject.

Another aspect of the invention relates to the use of the bacterial species *Roseburia hominis* in the preparation of a nutritional supplement or medicament for regulating the adaptive immune system of a subject.

Another aspect of the invention relates to the use of the bacterial species *Roseburia hominis* in the preparation of a nutritional supplement or medicament for regulating appetite in a subject.

Another aspect of the invention relates to a method of treating a disorder selected from an inflammatory disorder, an immune disorder and an intestinal disorder in a subject, said method comprising administering to the subject a nutritionally or pharmaceutically effective amount of the bacterial species *Roseburia hominis*.

Another aspect of the invention relates to a method of improving intestinal microbiota in a subject, said method comprising administering to the subject a composition comprising the bacterial species *Roseburia hominis*.

Another aspect of the invention relates to method of regulating the innate immune system of a subject, said method comprising administering to the subject a composition comprising the bacterial species *Roseburia hominis*.

Another aspect of the invention relates to a method of regulating the adaptive immune system of a subject, said method comprising administering to the subject a composition comprising the bacterial species *Roseburia hominis*.

Another aspect of the invention relates to a method of regulating appetite in a subject, said method comprising administering to the subject a composition comprising the bacterial species *Roseburia hominis*.

Another aspect of the invention relates to the bacterial species *Roseburia hominis* for use in medicine.

Another aspect of the invention relates to a pharmaceutical composition comprising the bacterial species *Roseburia hominis* and a pharmaceutically acceptable excipient, carrier or diluent.

Another aspect of the invention relates to a nutritional supplement comprising the bacterial species *Roseburia hominis* and a nutritionally acceptable excipient, carrier or diluent.

Another aspect of the invention relates to a probiotic composition comprising the bacterial species *Roseburia hominis*.

Another aspect of the invention relates to a feedstuff, food product, nutritional supplement, dietary supplement or food additive comprising the bacterial species *Roseburia hominis*.

Another aspect of the invention relates to a process for producing a pharmaceutical composition according to the invention, said process comprising admixing the bacterial species *Roseburia hominis* with a pharmaceutically acceptable excipient, carrier or diluent.

Another aspect of the invention relates to a process for producing a nutritional supplement according to the invention, said process comprising admixing the bacterial species *Roseburia hominis* with a nutritionally acceptable excipient, carrier or diluent.

Another aspect of the invention relates to the bacterial species *Roseburia hominis* for use in maintaining immune homeostasis in a subject.

DETAILED DESCRIPTION OF THE INVENTION

As mentioned above, one aspect of the invention relates to *Roseburia hominis* for use in one or more of:
treating an immune disorder;
treating an intestinal disorder;
improving intestinal microbiota;
regulating the innate immune system of a subject
regulating the adaptive immune system of a subject;
promoting Tregs and immune tolerance;
regulating appetite in a subject;
promoting gut health in a subject; and/or
maintaining immune homeostasis in a subject.

*Roseburia hominis*

*Roseburia hominis*, a recently described commensal-gut anaerobe of the phylogenetic cluster XIVa within the Firmicutes phylum, belongs to a dominant group of bacteria in the human gut and is also a major butyrate producer (11). The present applicant has elucidated the complete genome sequence and annotation for this bacterium. Further studies investigated both bacterial and host transcriptome responses in germfree mice mono-colonized with *R. hominis*. The roles of bacterial genes participating in colonization and adaptation to the murine gut, as well as the host genes responding to colonization by this bacterium are described herein.

Experiments by the Applicant have shown that the activity of *Roseburia hominis* is highly specific. Studies have shown that important genomes of *Roseburia* species are very different, indicating diverse functionality. Indeed, experiments have shown that bacteria from *Clostridium* Cluster XIVa, including the bacterial species *Roseburia intestinalis*, *Roseburia hominis* and *Eubacterium rectale* (all of which are butyrate producers) surprisingly induce very different and distinct effects on gut cells.

In one preferred embodiment, the bacterial species is the strain deposited under the terms of the Budapest Treaty at National Collections of Industrial, Food and Marine Bacteria (NCIMB) at NCIMB Ltd, Ferguson Building, Craibstone Estate, Bucksburn, Aberdeen, UK, AB21 9YA, on 21 Oct. 2004 on behalf of the Rowett Research Institute of Nutrition and Health, University of Aberdeen, Greenburn Road, Aberdeen, AB21 9SB, Scotland, UK, under the accession number NCIMB $14029^T$ *Roseburia hominis* A2-$183^T$ (DSM=$16839^T$).

The bacterial species is preferably *Roseburia hominis* as described in Duncan, S. H., Aminov, R. I., Scott, K. P., Louis, P., Stanton, T. B., & Flint, H. J. (2006) *Int. J. Syst. Evol. Microbial.* 56: 2437-2441.

In one preferred embodiment, the bacterial species is in the form of a live bacterial population, a lyophilized bacterial population, a non-viable bacterial preparation, or the cellular components thereof. Preferably, where the bacterial species is in the form of a non-viable bacterial preparation, it is selected from heat-killed bacteria, irradiated bacteria and lysed bacteria.

In one preferred embodiment, the bacterial species is in the form of live bacteria or the cellular components thereof.

In one preferred embodiment, the bacterial species is in isolated form. As used herein, the term "isolated" means isolated from its native environment.

In one preferred embodiment, the bacterial species is in biologically pure form. As used herein the term "biologically pure" refers to a laboratory culture that is substantially free from other species of organism. Preferably, the bacterial species is in the form of a culture of a single species of organism.

The invention also encompasses the use of mutants of the bacterial species or strains described herein. As used herein, the term "mutant" includes derived bacterial strains having at least 93% homology, preferably at least 96% homology, more preferably 98% homology to the polynucleotide sequence of a referenced strain, but otherwise comprising mutations in other sequences in the bacterial genome. Mutants are obtainable by genetic engineering techniques inferring alteration of the genetic material of the strains of the invention or inferring a recombination of the genetic material of the strains of the invention with other molecules. Typically, in order to obtain such mutant strains, a person skilled in the art can use standard mutagenesis techniques such as UV radiation or exposure to mutagenic chemical products.

As used herein, the term "mutations" includes natural or induced mutations comprising at least single base alterations including deletions, insertions, transversions, and other modifications known to those skilled in the art, including genetic modification introduced into a parent nucleotide or amino acid sequence whilst maintaining at least 50% homology to the parent sequence. Preferably, the sequence comprising the mutation or mutations has at least 60%, more preferably at least 75%, more preferably still 85% homology with the parental sequence. As used herein, sequence "homology" can be determined using standard techniques known to those skilled in the art. For example, homology may be determined using the on-line homology algorithm "BLAST" program, publicly available at http)://www.ncbi.nlm.nih.gov/BLAST/.

The invention also encompasses the use of homologues of the bacterial species or strains described herein. As used herein the term "homologue" refers to a bacterial strain having a nucleotide sequence having a degree of sequence identity or sequence homology with the nucleotide sequence of the parent bacterial strain (hereinafter referred to as a "homologous sequence(s)"). Here, the term "homologous" means an entity having a certain homology with the subject nucleotide sequence. Here, the term "homology" can be equated with "identity".

In the present context, a homologous sequence is taken to include a nucleotide sequence which may be at least 50, 60, 70, 75, 80, 85 or 90% identical, preferably at least 95%, 97%, 98% or 99% identical to the nucleotide sequence of the parent bacterial strain (the subject sequence).

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbial Lett 1999 17 4(2): 24 7-50; FEMS Microbial Lett 1999 177(1): 187-8), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60). Preferably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides. Preferably, the degree of identity with regard to a nucleotide sequence may be determined over the whole sequence.

The traditional identification of bacteria on the basis of phenotypic characteristics is generally not as accurate as identification based on genotypic methods. Comparison of the bacterial 16S rRNA gene sequence has emerged as a preferred genetic technique and allows for new strains to be identified by comparison of sequences with known bacterial DNA sequences using BLAST (http://blast.ncbi.nlm.nih.gov/Blast.cgi). The 16S rRNA gene sequence is universal in bacteria, and so relationships can be measured across many different bacteria. In general, the comparison of the 16S rRNA sequence allows differentiation between organisms at the genus level across all major phyla of bacteria, in addition to classifying strains at multiple levels, including species and sub-species level. The 16S rRNA gene sequence has been determined for a large number of strains. GenBank, the largest databank of nucleotide sequences, has over 20 million deposited sequences, of which over 90,000 are of 16S rRNA genes. This means that many previously deposited sequences exist against which the sequence of an unknown strain can be compared.

As used herein the term "16S rRNA identity" refers to the percentage identity with a known bacterial strain. In one preferred embodiment, the bacterial strain has a 16S rRNA identity of at least 99.5% with the strain deposited under the above accession number.

The invention also encompasses mutant strains, which can be obtained from the above-mentioned deposited strain, and strains exhibiting a DNA-DNA homology of at least 70% and/or a 16S RNA identity of at least 99.5% with the strain deposited under the above accession number.

In the context of the present invention, the term "DNA-DNA homology" refers to how closely related two or more separate strands of DNA are to each other, based on their nucleotide sequence. Typically, this is measured in terms of their % identity. In one preferred embodiment, the bacterial strain has a DNA-DNA homology of at least 70% with the strain deposited under the above accession number.

In one highly preferred embodiment, the bacterial strain has a DNA-DNA homology of at least 70% and a 16S rRNA identity of at least 99.5% with the strain deposited under the above accession number.

Therapeutic Applications

Another aspect of the invention relates to the bacterial species *R. hominis* for use in medicine.

More particularly, the bacterial species *Roseburia hominis* is for use in treating a disorder selected from an inflammatory disorder, an immune disorder and an intestinal disorder in a subject.

As used herein, the term "medicament" encompasses medicaments for both human and animal usage in human and veterinary medicine. In addition, the term "medicament" as used herein means any substance, which provides a therapeutic and/or beneficial effect. The term "medicament" as used herein is not necessarily limited to substances, which need Marketing Approval, but may include substances which, can be used in cosmetics, nutraceuticals, food (including feeds and beverages for example), probiotic cultures, nutritional supplements and natural remedies. In addition, the term "medicament" as used herein encompasses a product designed for incorporation in animal feed, for example livestock feed and/or pet food.

In one preferred embodiment of the invention, the disorder is selected from irritable bowel syndrome (IBS), colitis, inflammatory bowel disorder (IBD), including Crohn's disease and ulcerative colitis, pouchitis, functional dyspepsia, functional constipation, functional diarrhoea (including antibiotic associated diarrhoea, traveler's diarrhoea and pediatric diarrhoea), functional abdominal pain, functional bloating, Epigastric Pain Syndrome, Postprandial Distress Syndrome, gastrointestinal reflux disease (GERD), autoimmune diseases such as diabetes, arthritis, multiple sclerosis and psoriasis allergies, atopic diseases e.g. atopic dermatitis, necrotising enterocolitis, other infections, and combinations thereof.

In one particularly preferred embodiment, the disorder is an inflammatory disorder. Preferably, the expression of pro-inflammatory genes is downregulated in the host subject. Further details of these studies are presented below.

More preferably, the inflammatory disorder is colitis, even more preferably, Crohn's disease, ulcerative colitis or pouchitis.

In one particularly preferred embodiment, the intestinal disorder is IBS. The precise pathophysiology of IBS remains to be elucidated. Recent studies have described mucosal inflammation and alterations in intestinal microbiota in IBS patients and a disease correlation with intestinal infections.

In one particularly preferred embodiment, the intestinal disorder is IBD. Preferably, the expression of barrier genes is enhanced in the host subject. Further details of these studies are presented below.

In one particularly preferred embodiment, the intestinal disorder is Crohn's disease.

In one particularly preferred embodiment, the disorder is an immune disorder. Preferably, the immune disorder is selected from ulcerative colitis, pouchitis, other autoimmune conditions including rheumatoid arthritis, psoriasis, multiple sclerosis, allergies, including coeliac disease, atopic dermatitis and rhinitis.

In one embodiment, the bacterial species *Roseburia hominis* is for use in regulating the immune system of a subject. Immune regulation by bacterial species is known to be highly species-specific (8). In particular, the immune regulatory effect of Cluster XIVa and VI bacteria is very complicated, and independent of butyrate production (41).

In one preferred embodiment, the innate immune system of the subject is modulated.

In another preferred embodiment, the adaptive immune system of the subject is modulated towards immune regulation (and not immune activation, therefore reducing inflammation).

Another aspect of the invention relates to the bacterial species *Roseburia hominis* for improving intestinal microbiota in a subject.

Intestinal microbiota refers to microorganisms that live in the digestive tract of the host animals. These microorganisms perform a wide variety of metabolic, structural, protective and other beneficiary functions. As used herein, "improving intestinal microbiota" refers to increasing the number and/or or type of microorganisms present in the intestine of a host, and/or increasing the activity of said microorganisms in terms of their metabolic, structural, protective and other beneficiary functions.

Preferably, *Roseburia hominis* colonizes the colon and/or the ileum, more preferably the colon.

In one preferred embodiment, *Roseburia hominis* regulates the expression of at least one mobilization or chemotaxis gene.

More preferably, *Roseburia hominis* upregulates the expression of at least one mobilization or chemotaxis gene. More preferably still, the mobilization or chemotaxis gene is selected from MobA and MobL.

In another preferred embodiment, *Roseburia hominis* regulates the expression of at least one gene selected from FlaA1, FlaA2, Fla3 and FlaB.

Specific serum antibodies to FLA type proteins are present in inflammatory bowel disease. Thus, in one preferred embodiment, the *Roseburia hominis* is for use in treating inflammatory bowel disease.

In another preferred embodiment, *Roseburia hominis* regulates the expression of one or more of the following: acetyl-CoA acetyltransferase, 3-hydroxyacyl-CoA dehydrogenase, butyryl-CoA dehydrogenase, electron transfer flavoprotein beta subunit, and electron transfer flavoprotein alpha subunit.

Another aspect of the invention relates to the bacterial species *Roseburia hominis* for regulating the innate immune system of a subject.

As used herein, the term "innate immune system", also known as the non-specific immune system, comprises the cells and mechanisms that provide the host with immediate defense against infection by other organisms in a nonspecific manner. This means that the cells of the innate system recognize and respond to pathogens in a generic way, but unlike the adaptive immune system, it does not confer long-lasting or protective immunity to the host.

As used herein, the term "regulating the innate immune system" means inducing the activity of the innate immune system, and/or increasing the level of activity relative to the baseline level of activity such that it promotes immune homeostasis.

Loss or dysregulation of the innate immune function, either due to loss of epithelial barrier, innate immune peptides such as defensins, chemokines and cytokines or defective TLR signalling are associated with increased risk of inflammatory diseases, in several body organs including the gut. Such diseases include inflammatory bowel disease. Thus, in one highly preferred embodiment, the *Roseburia hominis* is for use in treating inflammatory bowel disease.

In one preferred embodiment, the *Roseburia hominis* regulates the expression of at least one gene selected from Tlr5, Tir1 Vnn1, Defb37, Pla2g, Muc16, Itln, Sprr1a, Cldn4, Pmp22, Crb3, Magi3, Marveld3, Mpp7, Defcr20, Pcgf2, Ltbp4, Igsf8 and Tcfe2a. Many of theses genes are gut barrier genes and antimicrobials and hence work to reduce invasiveness of gut pathogens and also reduce the numbers of viable pathogens.

Another aspect of the invention relates to the bacterial species *Roseburia hominis* for regulating the adaptive immune system of a subject.

As used herein, the term "adaptive immune system", otherwise known as the "specific immune system" refers to highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered.

As used herein, the term "regulating the adaptive immune system" means inducing the activity of the adaptive immune system, and/or promoting immune homeostatic mechanisms by increasing the level of activity relative to the baseline level of activity. Preferably, the adaptive immune system is modulated towards immune regulation (and not immune activation therefore reducing inflammation).

Defects and disorders associated with the adaptive immune system, particularly related to the function of T cells, are associated with many inflammatory and autoimmune diseases. T cell responses associated with Th1, Th2 and Th17 are associated with atopic, inflammatory and autoimmune diseases. Therapies which improve or increase T regulatory (Tregs) cell populations are important in controlling diseases driven by excessive Th1, Th2 and Th17 cell responses.

In one preferred embodiment, *Roseburia hominis* activates at least one immune response gene in the colon or ileum.

In one preferred embodiment, *Roseburia hominis* regulates the adaptive immune system by modulating the expression of genes associated with T-cell regulation, more preferably in the colon. More preferably, *Roseburia hominis* induces Tregulatory cells (Tregs). An increase in Treg numbers will combat the effects of other effector T cells, such as Th1, Th17 and Th2 which drive inflammation, autoimmunity and allergic/atopic conditions. Hence this property of *R. hominis* can be exploited to address many diseases where Teff/Treg cell balance is lost, e.g. Crohn's and ulcerative colitis In one particularly preferred embodiment, *Roseburia hominis* upregulates the expression of at least one gene selected from Ly6g6c and Ly6g6e in the ascending colon. Depletion of Ly6g6c and Ly6g6e increases infection risk, both gut and respiratory tract and is associated with diseases such aa neutropenia. Thus, in one preferred embodiment, the *Roseburia hominis* is for use in treating neutropenia.

Another aspect of the invention relates to the bacterial species *Roseburia hominis* for use in maintaining immune homeostasis in a subject. As used herein "maintaining immune homeostasis" refers to the self-regulation of the body's immune system to maintain oral tolerance or immune stability in response to changing conditions. Oral tolerance refers to the normal immune responses to food and commensal bacteria in a healthy gut. These are lost in coeliac disease and Inflammatory Bowel Diseases such as Crohn's disease and ulcerative colitis. Thus, in one particularly preferred embodiment, *Roseburia hominis* is for use in treating coeliac disease and Inflammatory Bowel Diseases such as Crohn's disease and ulcerative colitis.

Another aspect of the invention relates to the bacterial species *Roseburia hominis* for use in regulating appetite in a subject.

As used herein, "regulating appetite" refers to the ability to modulate (i.e. increase or decrease) the desire for a host to eat food. Preferably, *Roseburia hominis* exerts a stimulatory effect on host appetite by downregulating the expression of genes associated with the suppression of appetite. Preferably, *Roseburia hominis* downregulates the expression of at least one gene selected from Agt, Cartpt, Cck, Cxcl12 and Gcg. More preferably, *Roseburia hominis* downregulates, the expression of the satiety hormones Cck and Gcg.

The bacterial species according to the invention may also be used in prophylactic applications. In prophylactic applications, bacterial species or compositions according to the invention are administered to a patient susceptible to, or otherwise at risk of, a particular disease in an amount that is sufficient to at least partially reduce the risk of developing a disease. Such an amount is defined to be "a prophylactic effective dose". The precise amounts depend on a number of patient specific factors such as the patient's state of health and weight

BRIEF DESCRIPTION OF THE DRAWINGS

The present invention is further described by way of the following figures, wherein.

Ascending colon (haematoxylin/eosin stained) of IL-10KO and *R. hominis* treated IL-10KO animals. Original magnification ×100.

Figure 7:
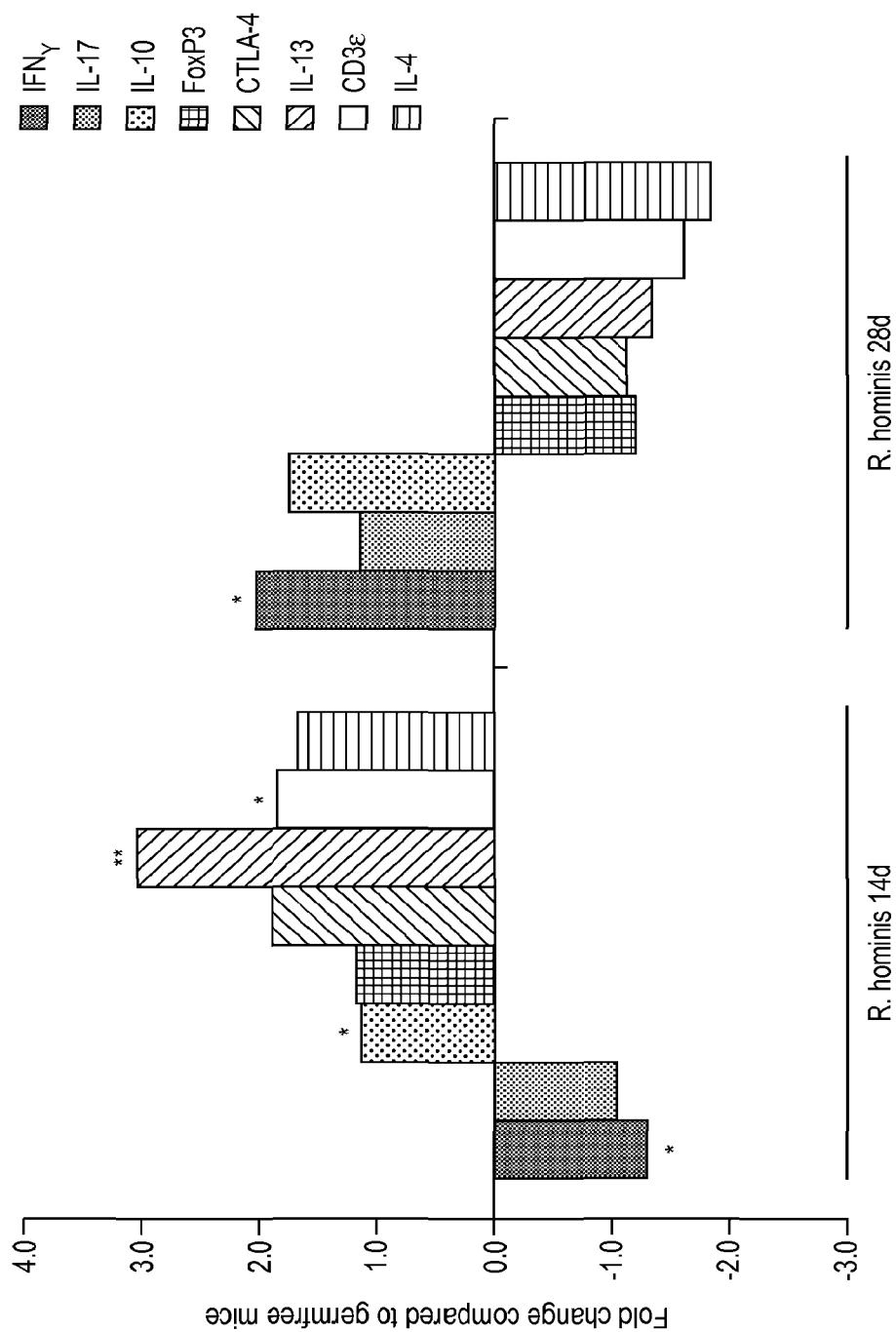

FIG. 7 shows real-time PCR analysis of mRNA levels of IL-10, IL-17 and IFN-γ. Real-time PCR was performed on ascending colon tissue for measurement of T cell markers. Real-time PCR results are means of triplicates, *P<0.05, **P<0.01.

Figure 8:
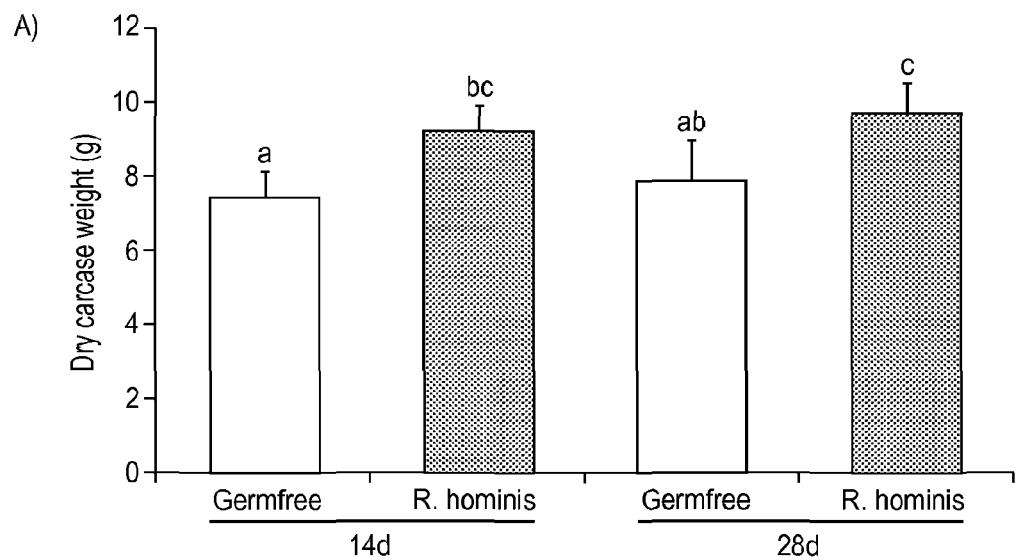
Figure 8:
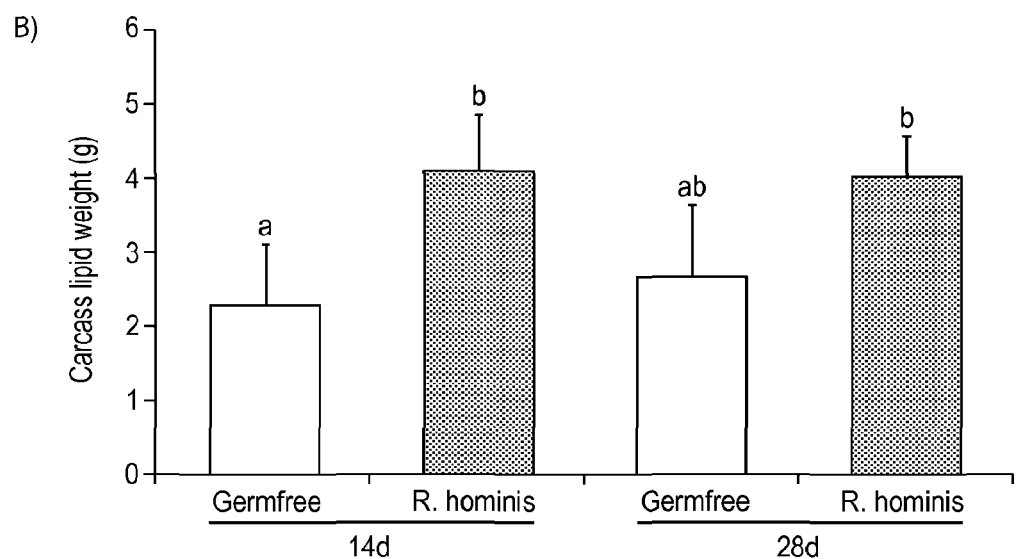

FIG. 8 shows the effects of mono-association of GF mice with *R. hominis* on body weight composition. Dry body weight and lipid carcass analysis was performed. (A) Dry carcass weights of *R. hominis*-associated mice were significantly heavier compared to GF animals. (B) Further carcass lipid analysis showed that total adiposity was also significantly higher in *R. hominis*-treated animals at 14 d.

Figures 9, 10:
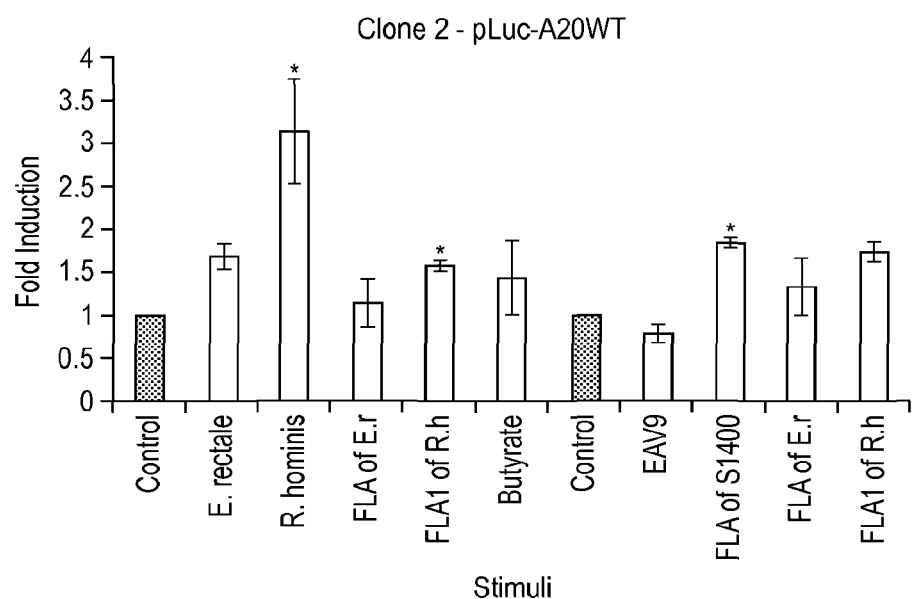

FIG. 9 illustrates a comparison of gene expression data for three strains of bacteria from Cluster XIVa (Firmicutes), namely *Roseburia hominis, E. rectale* and *Roseburia intestinalis*.

FIG. 10 shows that *Roseburia hominis* induces A20, a negative regulator of NF-KB signaling with potent anti-inflammatory activity, whereas other bacterial strains have no effect. The flagellin moiety of *Roseburia hominis* (FLA1 of *R. hominis*) also induces A20 unlike that of *Eubacterium rectale*, a related bacterium. In more detail, FIG. 10 shows the fold-induction of A20 for *E. rectale, R. hominis*, FLA of *E. rectale*, FLA1 of *R. hominis*, EAV9, FLA of SV1400 relative to controls.

Figure 11:
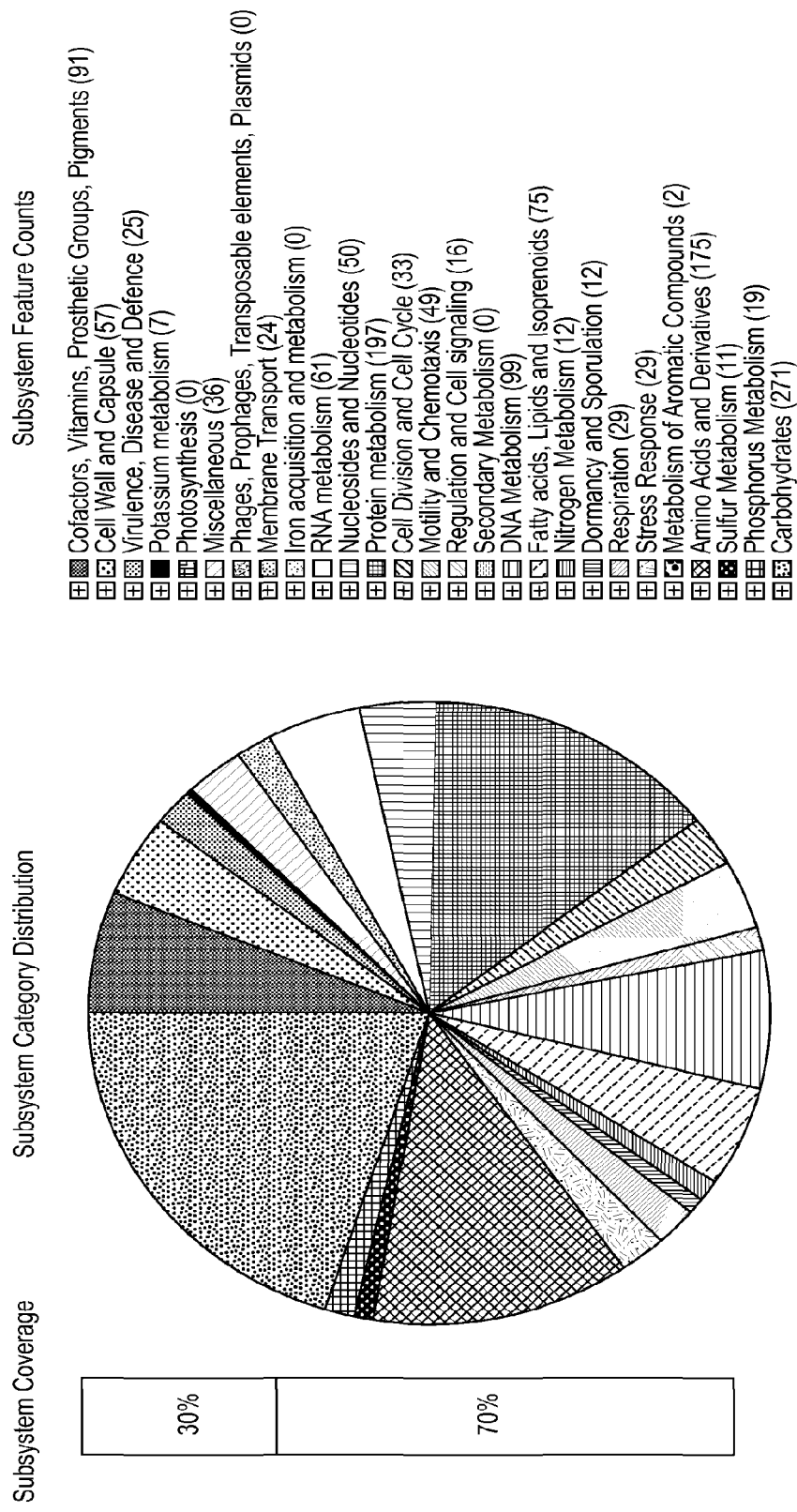

FIG. 11 shows the Subsystem Category Distribution for *R. hominis* A2-183 as determined by RAST, showing functional subsystems and the number of genes in each subcategory.

Figure 12:
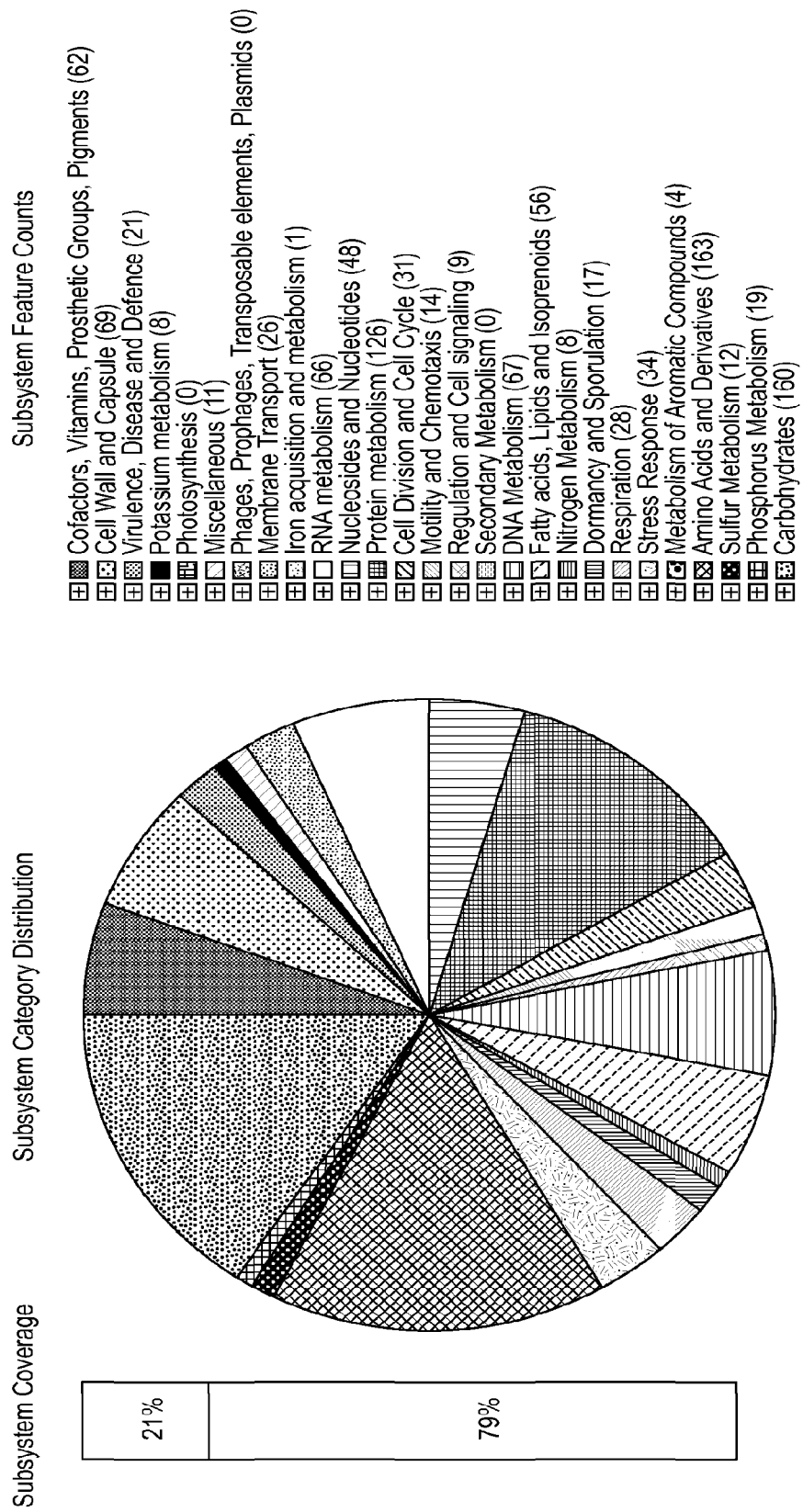

FIG. 12 shows the Subsystem Category Distribution for *R. inulinivorans* DSM 16841 A2-183 as determined by RAST, showing functional subsystems and the number of genes in each subcategory.

Figure 13:
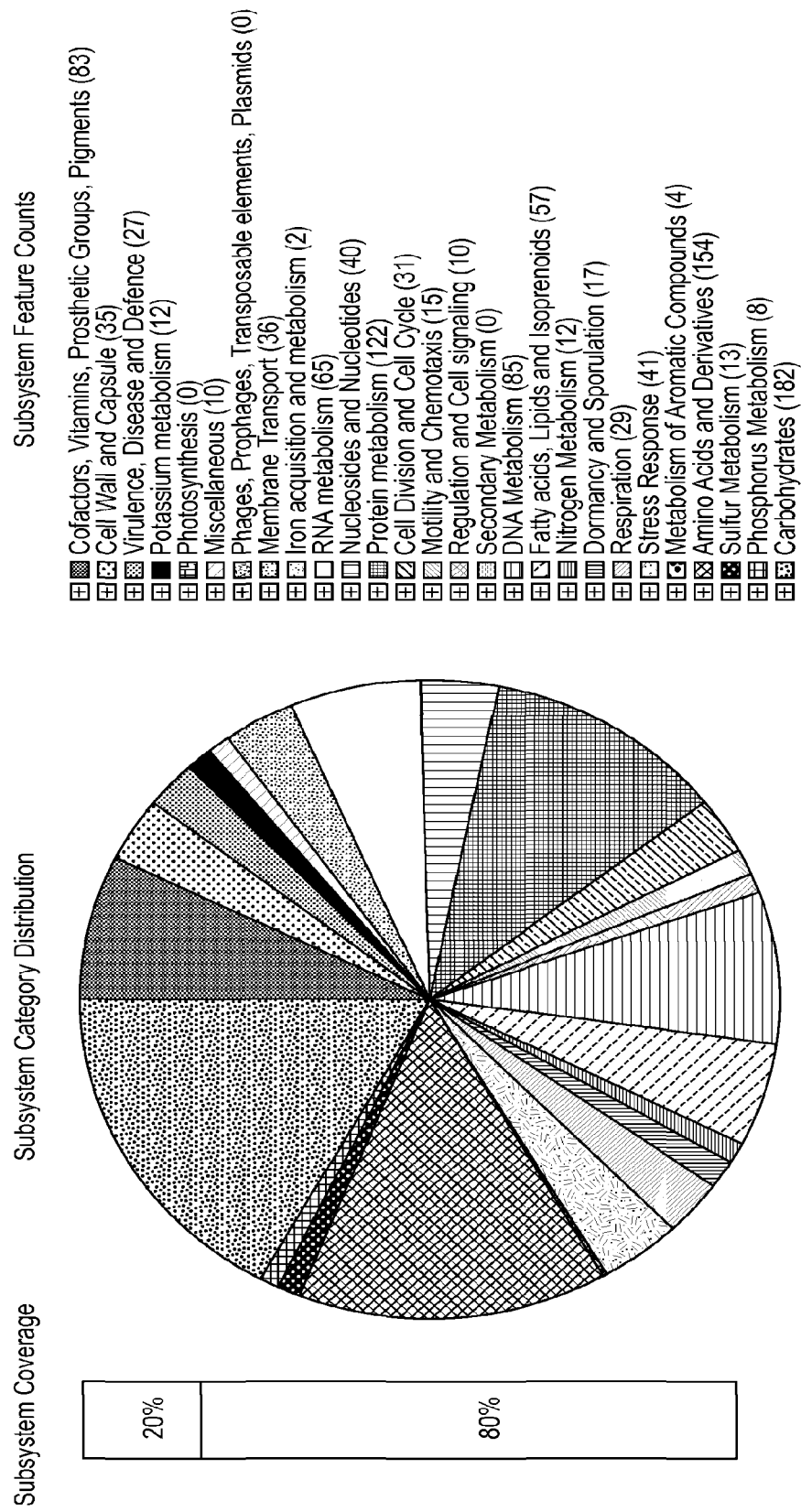

FIG. 13 shows the Subsystem Category Distribution for *R. intestinalis* L1-82 as determined by RAST, showing functional subsystems and the number of genes in each subcategory.

Figure 14:
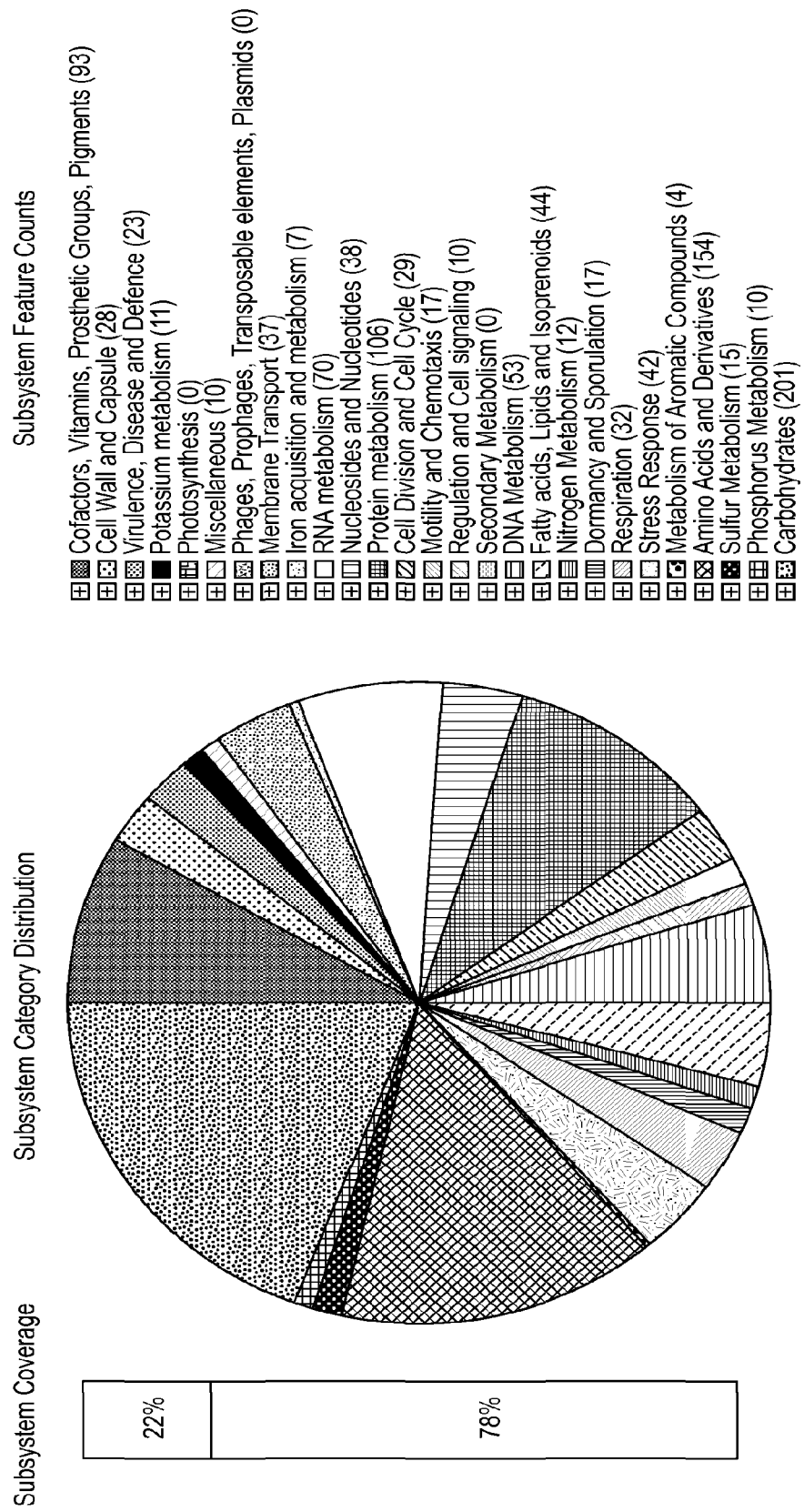

FIG. 14 shows the Subsystem Category Distribution for *R. intestinalis* M50/1 as determined by RAST, showing functional subsystems and the number of genes in each subcategory.

Figure 15:
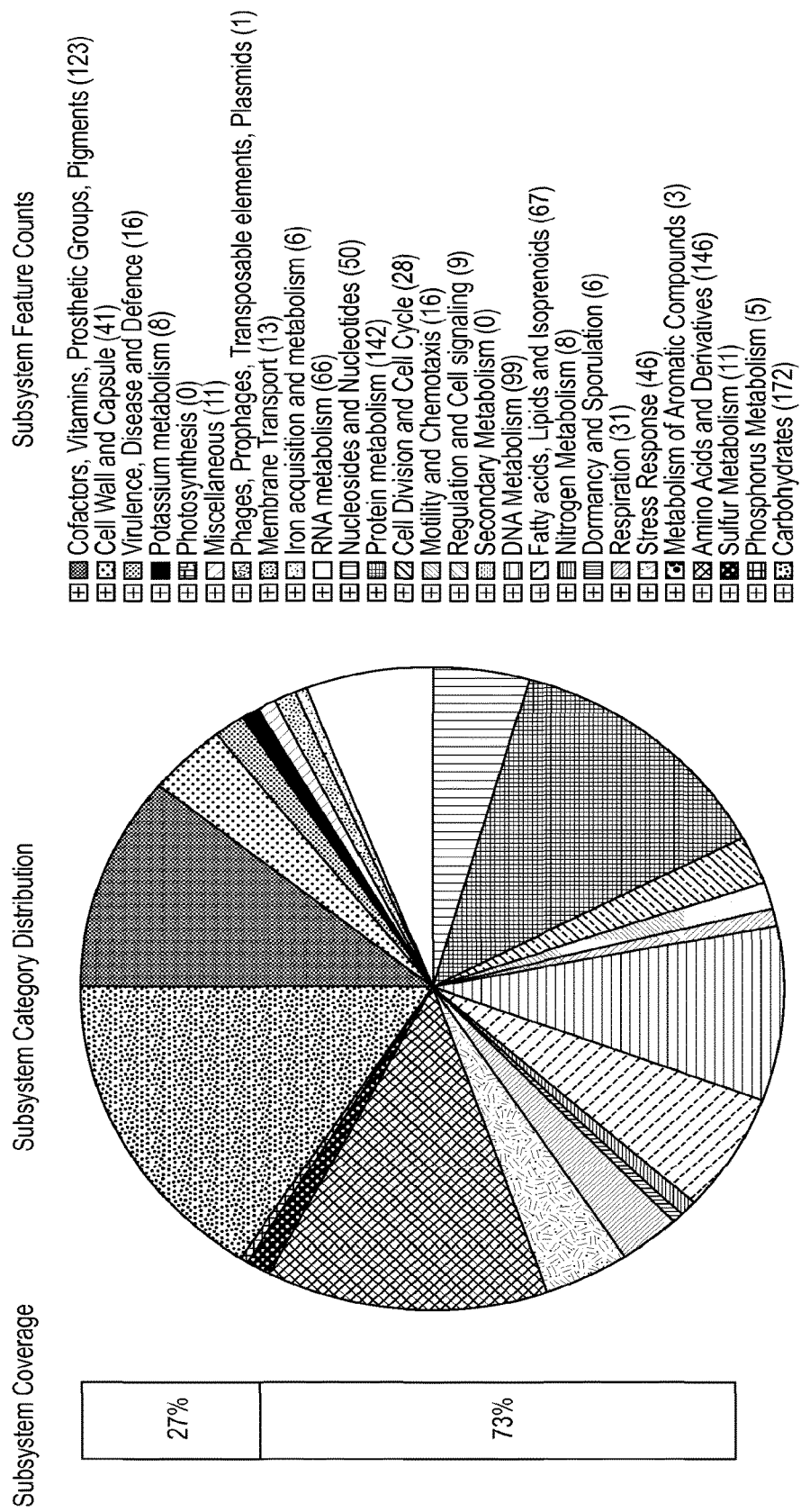

FIG. 15 shows the Subsystem Category Distribution for *Eubacterium rectale* ATCC 33656 as determined by RAST, showing functional subsystems and the number of genes in each subcategory.

*R. HOMINIS* PREFERENTIALLY COLONIZES THE COLON

Figure 1:
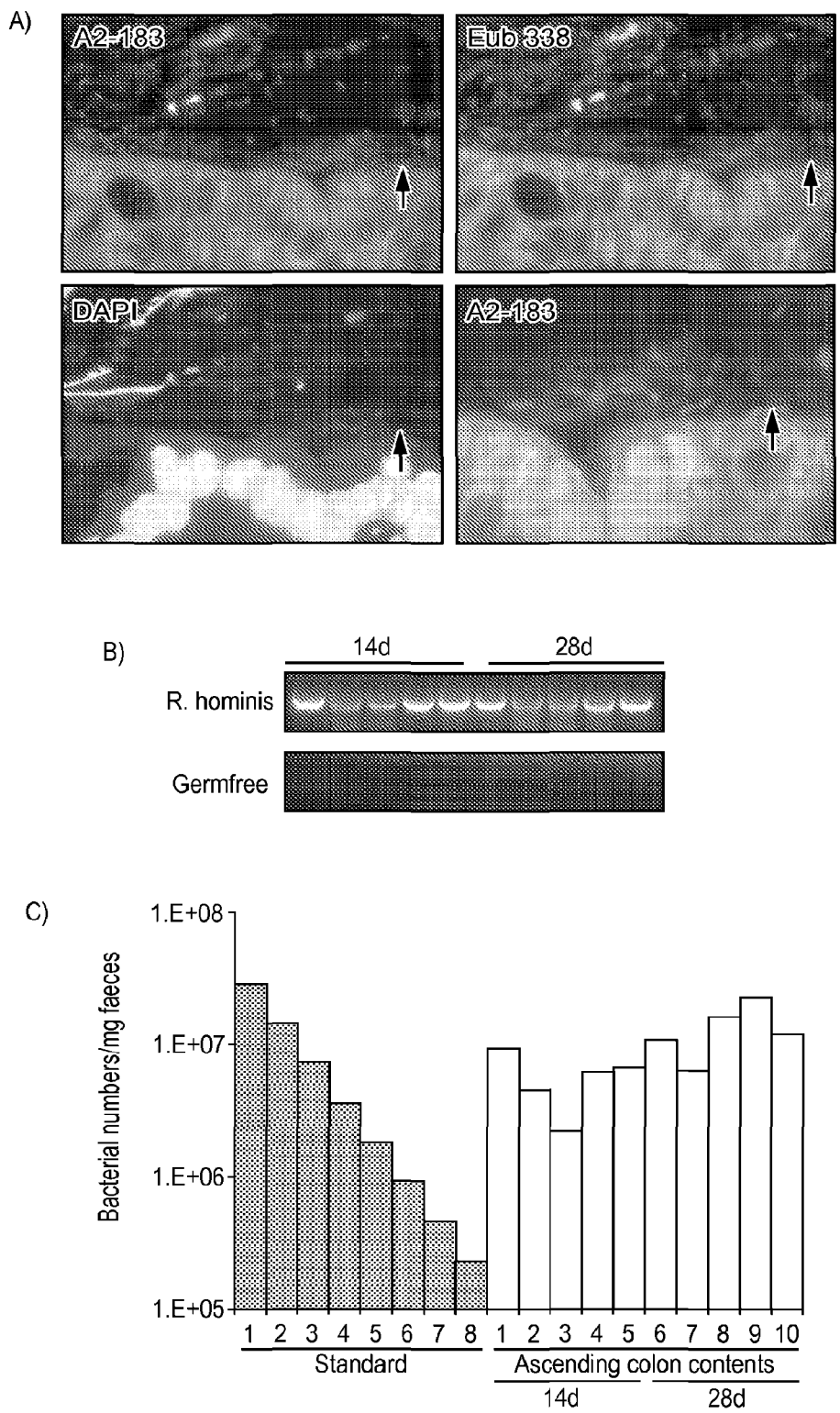
FIG. 1 shows the abundance and localization of *R. hominis* in ascending colon. (A) *R. hominis*-colonized mouse ascending colon showing close association of bacteria with the host epithelium, using the A2-183 FISH probe. Original magnification ×630. (B) PCR using *R. hominis*-specific primers showed a strong positive signal in faecal DNA post-colonization, while faeces of GF animals were negative for the presence of any bacteria. (C) Real-time PCR analysis showing colonization levels of *R. hominis*/mg faeces.
Figure 2:
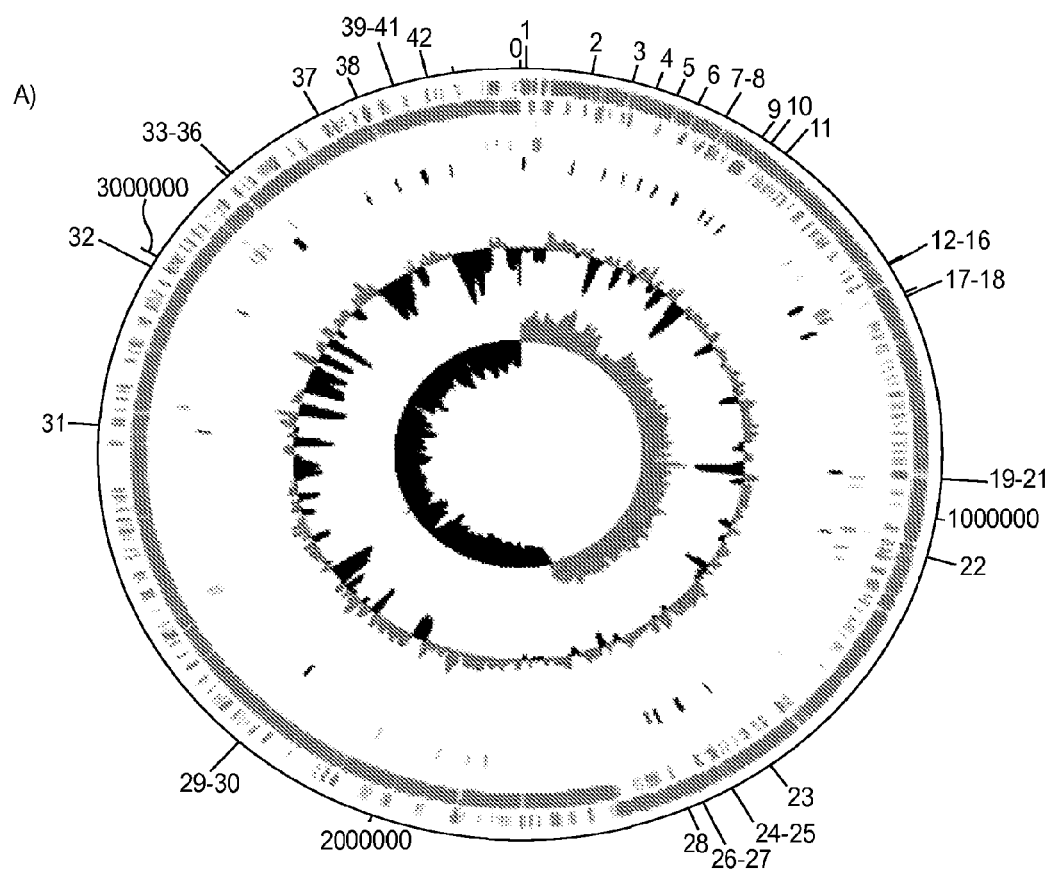
FIG. 2 shows the sequence and annotation of *R. hominis* genome. (A) *R. hominis* circular genome map with the location of the PCR experiments indicated in the regions targeted by the primers. The tracks on the genome map, starting at the outer track 0, are: track 0—(blue) Real-time PCR experiments indicated by numbered tick marks; track 1—(pale blue) Forward CDS; track 2—(pale blue) Reverse CDS; track 3—(blue) rRNA; track 4—(green) tRNA; track 5—(red) STS marking regions targeted by Real-time PCR; graph 1—GC content; graph 2—GC bias. (B) Functional annotation of the *R. hominis* genome.
Figure 2:
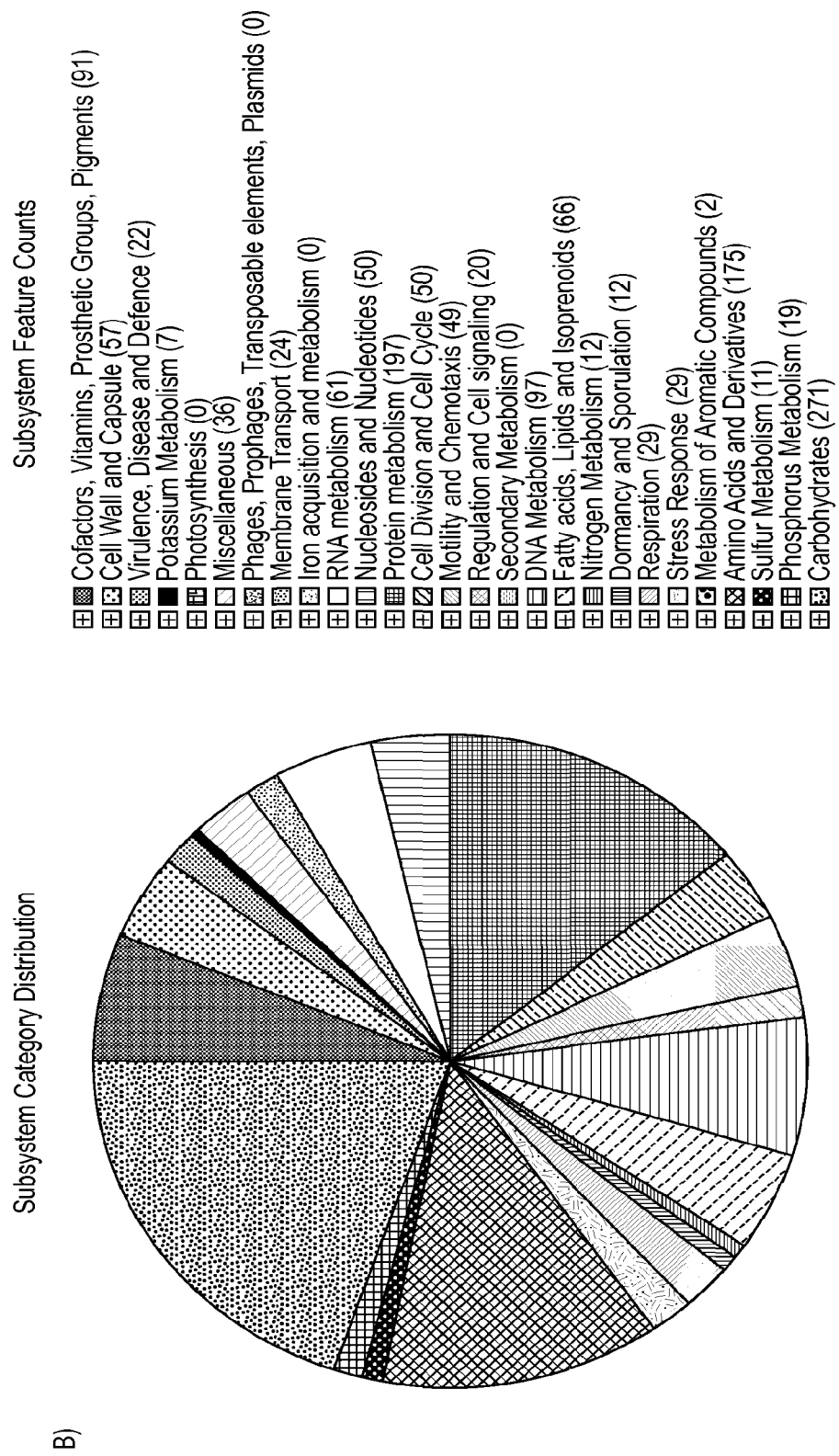

Healthy adult C3H/HeN germfree (GF) mice were inoculated with three gavages of *R. hominis* on consecutive days. Successful colonization was achieved using an inoculation medium containing 3% ascorbic acid and 2% cysteine to protect the bacterium from oxygen exposure. Analysis of gut tissue by fluorescent in situ hybridization (FISH) revealed that *R. hominis* colonized both the ileum and colon, but was found in much higher numbers in the colon. Bacteria were also found closely associated with the colonic mucosa (FIG. 1A). Colonization was further validated and quantified by PCR using *R. hominis*-specific primers with numbers approximating 1×1010 bacteria/g faeces (FIGS. 1B and 1C). Faeces of GF animals tested negative for the presence of any bacteria. The *R. hominis* Genome Reveals Unique Genes Promoting Host Interactions The complete genome sequence of *R. hominis* A2-183 was elucidated (FIG. 2A, which is represented by a single 3,592,125-bp chromosome (FIG. 2B). Automated and manual annotation of the genome using the RAST platform revealed the presence of four ribosomal operons, 66 RNAs and 3,273 predicted proteins. The largest group of genes belonged to the Subsystem Category Carbohydrates (271 genes), encoding proteins involved in carbohydrate metabolism, followed by Protein Metabolism (197) and Amino acids and Derivatives (175) (FIG. 2B). Other important functional categories included Motility and Chemotaxis (49) and Dormancy and Sporulation (12). Comparative genomic analysis established that the closest relative in terms of genomic structure and function among the complete bacterial genomes is *Eubacterium rectale* (12), which is not surprising given the close taxonomical relatedness of these organisms (11, 13). Comparative reconstruction of these two genomes with 1,095 genes revealed that they differed by approximately 25% of the genes. In particular, these differences encompassed genes encoding important functions for interaction with the host. For example, the Motility and Chemotaxis genes encoding type IV fimbrial assembly proteins PilB and PilC were present in *E. rectale* but absent in *R. hominis* whereas flagellar basal-body rod protein FlgC, flagellar hook-basal body complex protein FliE, flagellin protein FlaB and flagellar motor switch protein FliG were unique to *R. hominis* The two bacterial genomes also differed by 42 carbohydrate genes, reflecting their divergent nutritional requirements. *R. hominis* Responds to the Gut Environment by Up-Regulating Mobilization and Chemotaxis Genes To determine the genes differentially expressed by *R. hominis* in response to association with the host and diet, a microarray was constructed using 6,000 PCR fragments from the small-insert-size sequencing library. Subsequent Realtime PCR validation was performed on 42 differentially expressed genes which cluster at specific regions of the *R. hominis* genome as illustrated in FIG. 2B. To distinguish between the effects of gut environment and dietary components, bacterial RNA was isolated from four different experimental conditions: (i) in vivo, from the caecum of mono-associated mice; (ii) in vitro, from bacteria grown in culture media; (iii) in vitro, from bacteria grown in the presence of dietary components; and (iv) from bacteria incubated on the surface of confluent Caco-2 and HT-29 cells.

Figure 3:
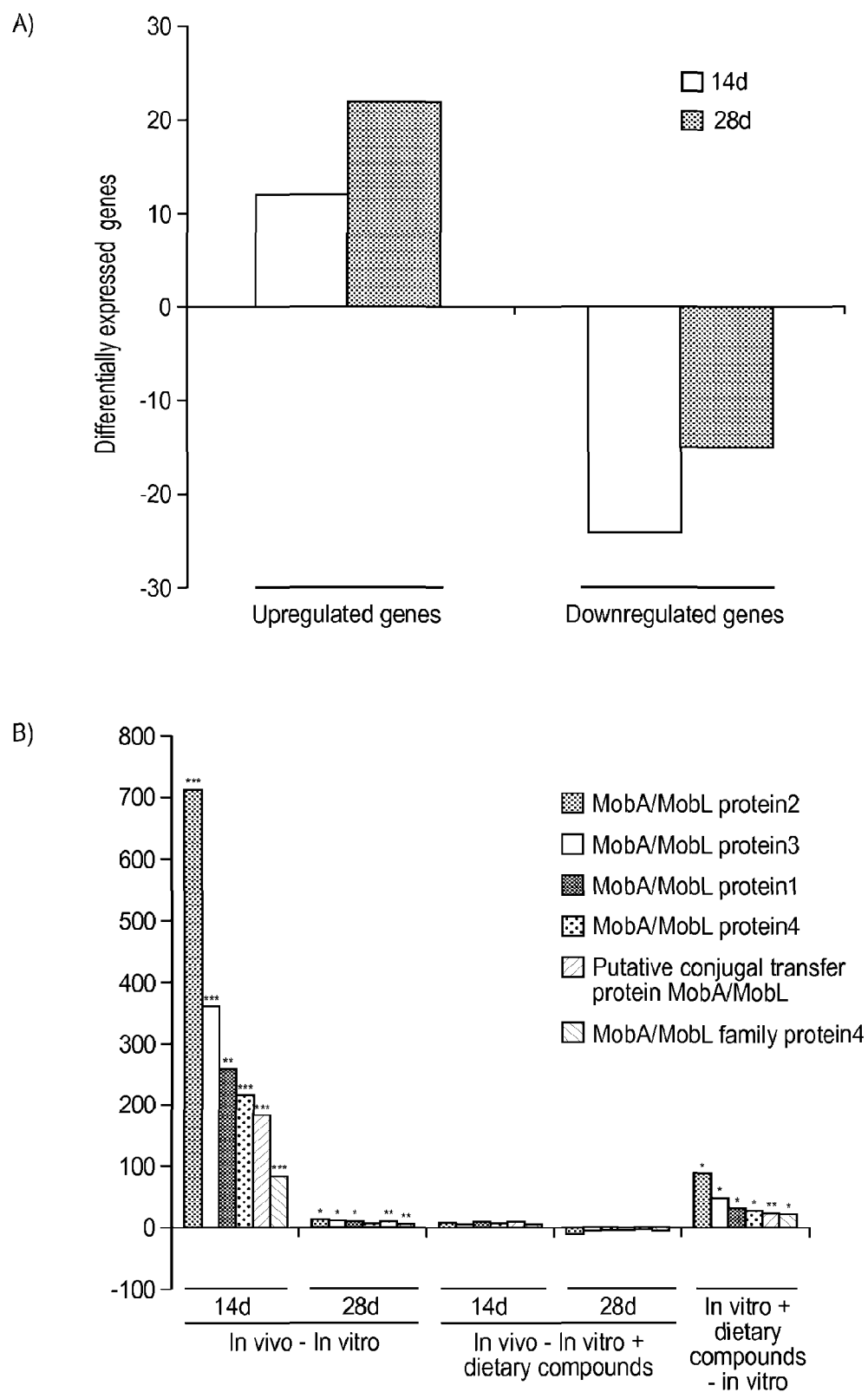
FIG. 3 identifies transcripts differentially expressed in *R. hominis* after colonization and adaptation to the murine gut. (A) Bacterial RNA was isolated from mouse caecum contents, labeled with either dCTP-Cy3 or dCTP-Cy5 during cDNA synthesis and hybridized to microarray slides incorporating a dye swap. Data was considered significant when fold change>2 and P<0.05. 50 differentially expressed genes (in vivo vs. in vitro) were uncovered by microarray analysis. (B) Real-time PCR validation of genes involved in conjugation/mobilization transfer. (C) Real-time PCR validation of genes involved in Motility and Chemotaxis. (D) Western blot of ascending gut contents immuno-stained with affinity-purified Fla2 antibody at 14 d (lane 1: ladder, lanes 2-6: gut contents from animals 1-5, lanes 7-8: empty, lanes 9-10: *R. hominis* biomass (positive control)). Picture of *R. hominis* showing flagella (black arrows) and (E) Real-time PCR validation of genes involved in butyrate metabolism. (F) Realtime PCR analysis of *R. hominis* transcripts during in vitro exposure to human intestinal epithelial cells. Real-time PCR results are means of triplicates, *P<0.05, P<0.01, *p<0.001.
Figure 3:
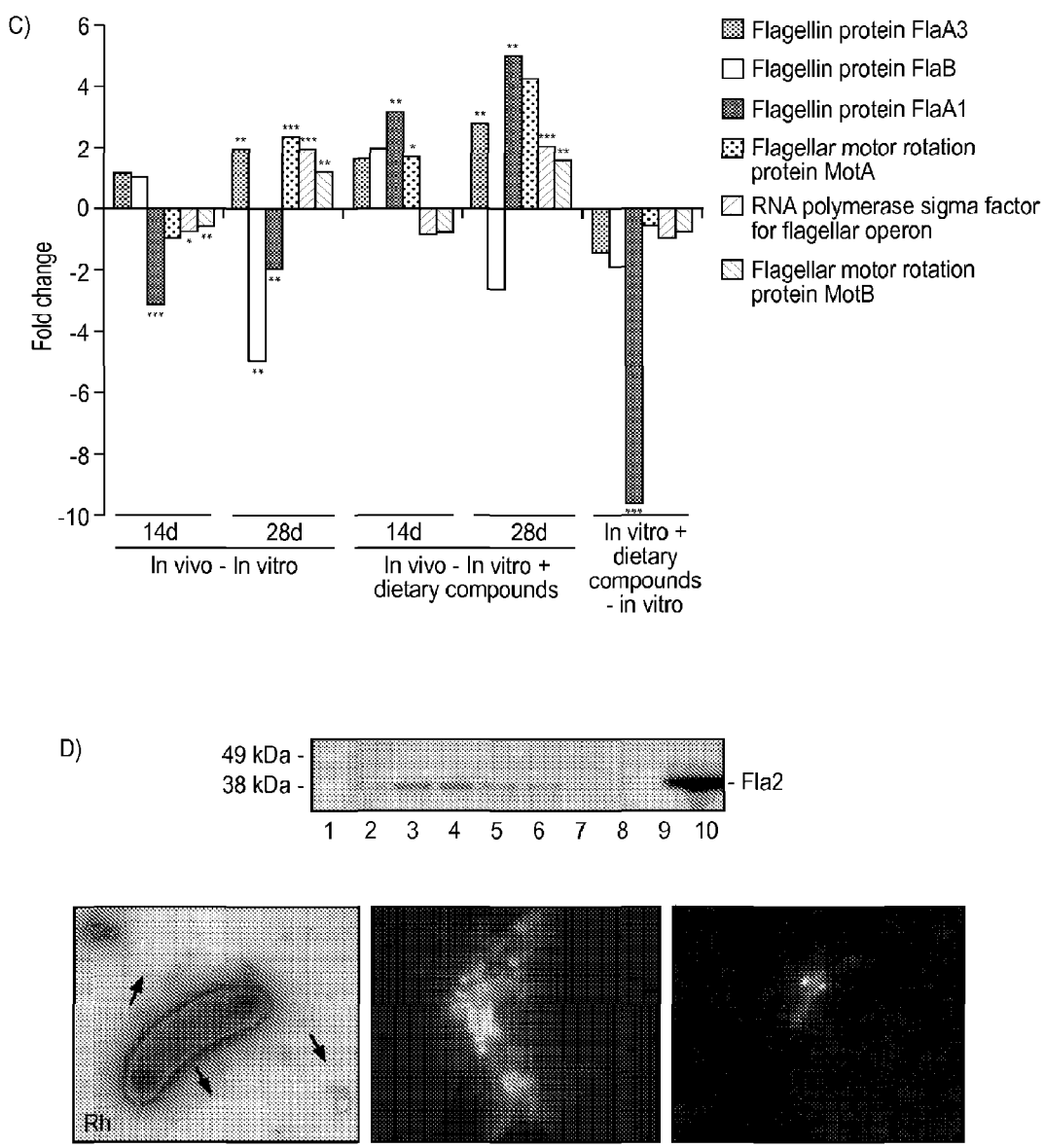
Figure 3:
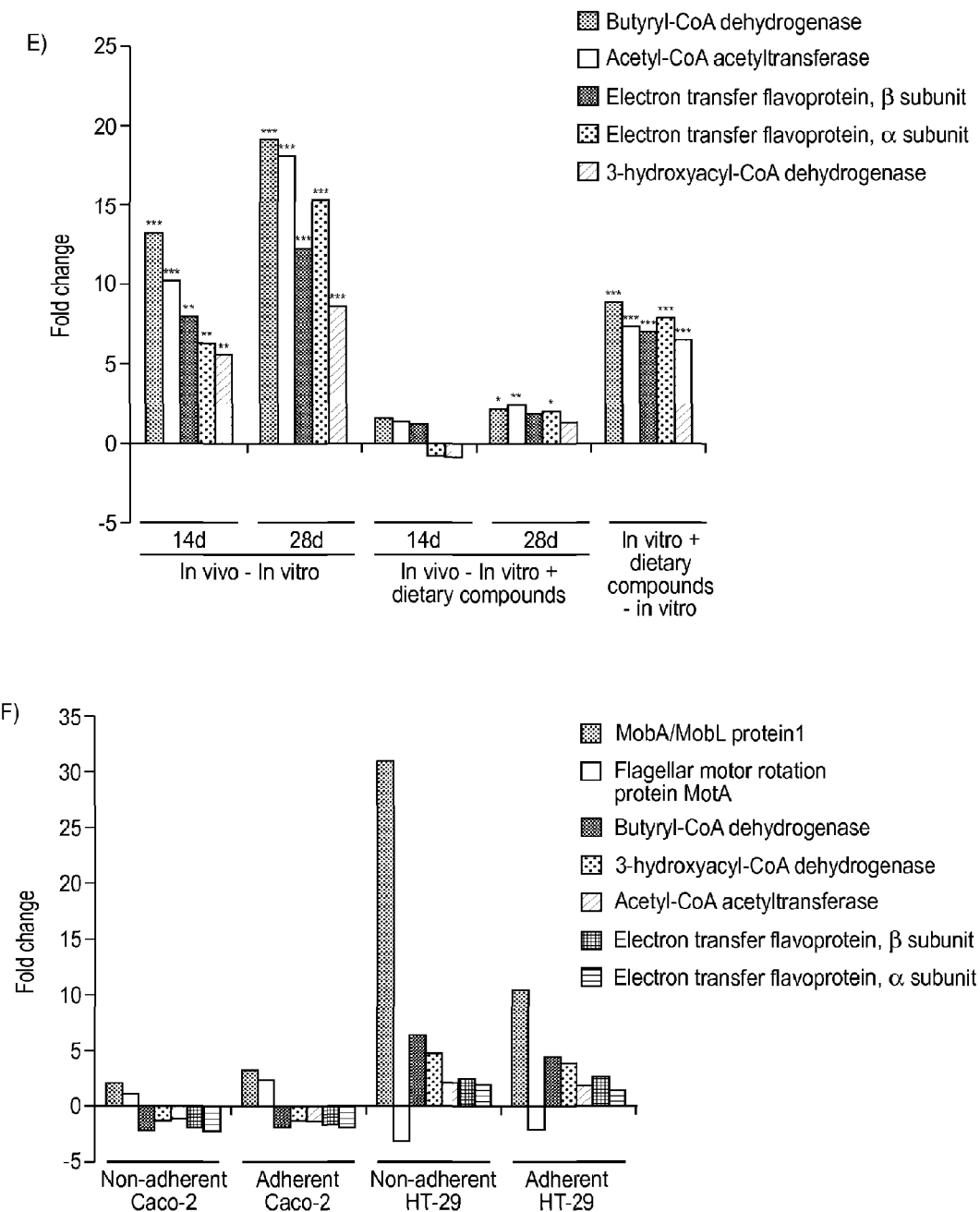

Fifty differentially expressed genes were identified (in vivo vs. in vitro) (FIG. 3A). The most surprising discovery was an extremely high up-regulation in vivo of genes involved in conjugation/mobilization transfer, the mobA- and mobL-like genes (FIG. 3B). The presence of such genes in the transcriptional studies was surprising as no identifiable genes were assigned to Phages, Prophages, Transposable Elements and Plasmids in the Subsystem Category feature. This difference in gene detection and allocation is likely due to the recognized limitations of the Subsystem Category annotation. The stimulatory effect of dietary compounds was much less pronounced, suggesting that the gut environment per se is a major inducer of genes involved in horizontal gene transfer.

Other gut environment-induced subsystems included Membrane Transport, in particular magnesium transport, and Motility and Chemotaxis including multiple methyl-accepting chemotaxis proteins and genes of the flagellar operon (FIG. 3C). *R. hominis* possesses multiple flagellin genes flaA1, flaA2, flaA3, and flaB and interestingly growth in the mouse gut environment promoted flagellin expression in this bacterium as seen by western-blotting of bacteria isolated from in vivo colonized mice using *R. hominis*-specific flagellin antibodies (FIG. 3D). This is consistent with previous reports indicating that only certain subsets of Firmicutes produce flagella in vivo (14).

Not surprisingly, the expression of catabolic metabolism genes in *R. hominis* in the gut environment was mostly affected by dietary compounds (FIG. 3E). The genes involved included acetyl-CoA acetyltransferase, 3-hydroxyacyl-CoA dehydrogenase, butyryl-CoA dehydrogenase and phosphoenolpyruvate carboxykinase [ATP]. Although the regulation of these genes was mostly diet-driven, at the later sampling point the host effect was also apparent. Unexpectedly, the host environment down-regulated some genes participating in the metabolism of host-derived substances such as glucuronate, which is common in carbohydrate chains of mucosal proteoglycans.

Figure 4:
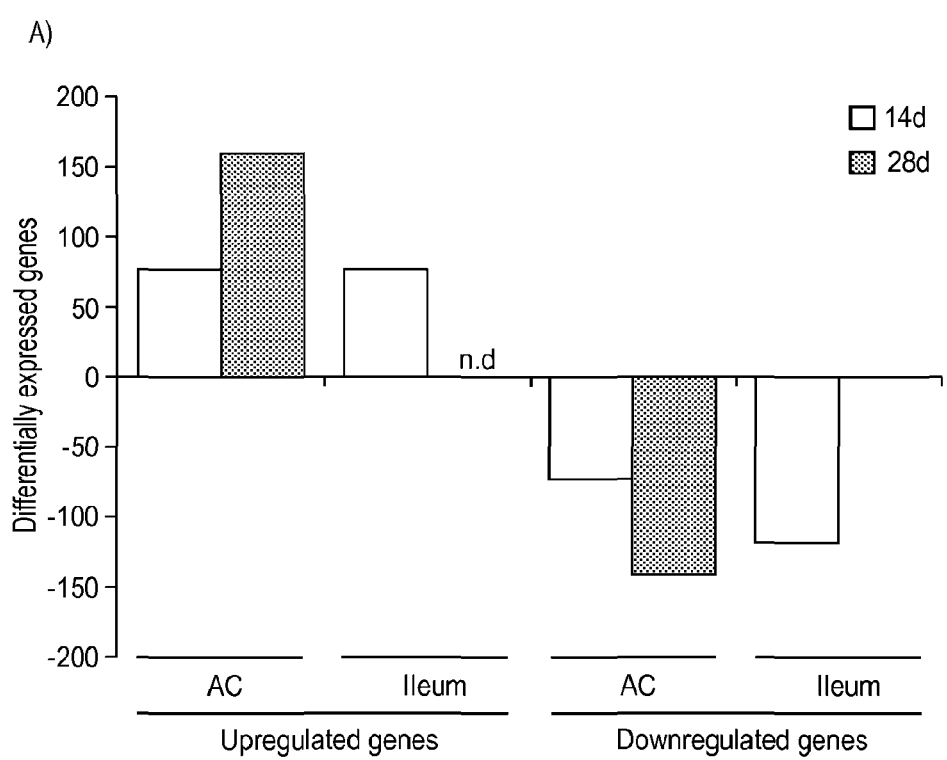
FIG. 4 identifies transcripts differentially expressed in the murine gut after mono-association with *R. hominis*. (A) Affymetrix microarray analysis of differentially expressed genes *R. hominis*-colonized mice relative to GF. Bar graphs represent number of genes higher and lower expressed after 14 and 28 days. (B) Heatmap generated from differentially expressed genes with functional significance-between GF and *R. hominis*-colonized mice at 14 d and 28 d. Columns represent individual arrays, and rows specific genes of interest. The Z-score depicts a measure of distance, in standard deviations, away from the mean. The relative value for each gene is depicted by colour intensity, with green indicating higher expression and red depicting lower expression. (C) Real-time PCR validation of genes shown to be significantly different between *R. hominis*-colonized and GF mice. Realtime PCR results are means of triplicates, *p<0.05, P<0.01, *P<0.001.
Figure 4:
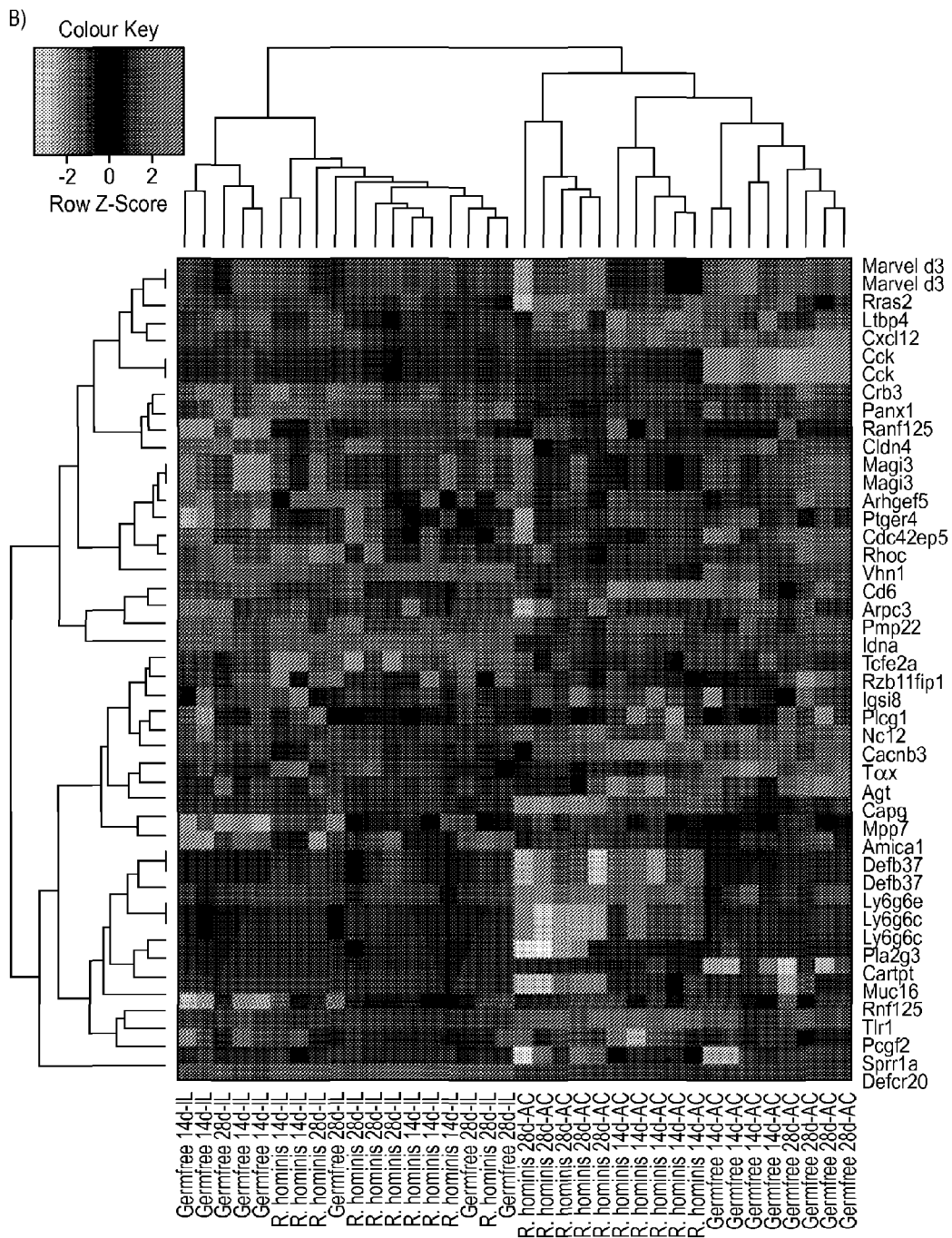
Figure 4:
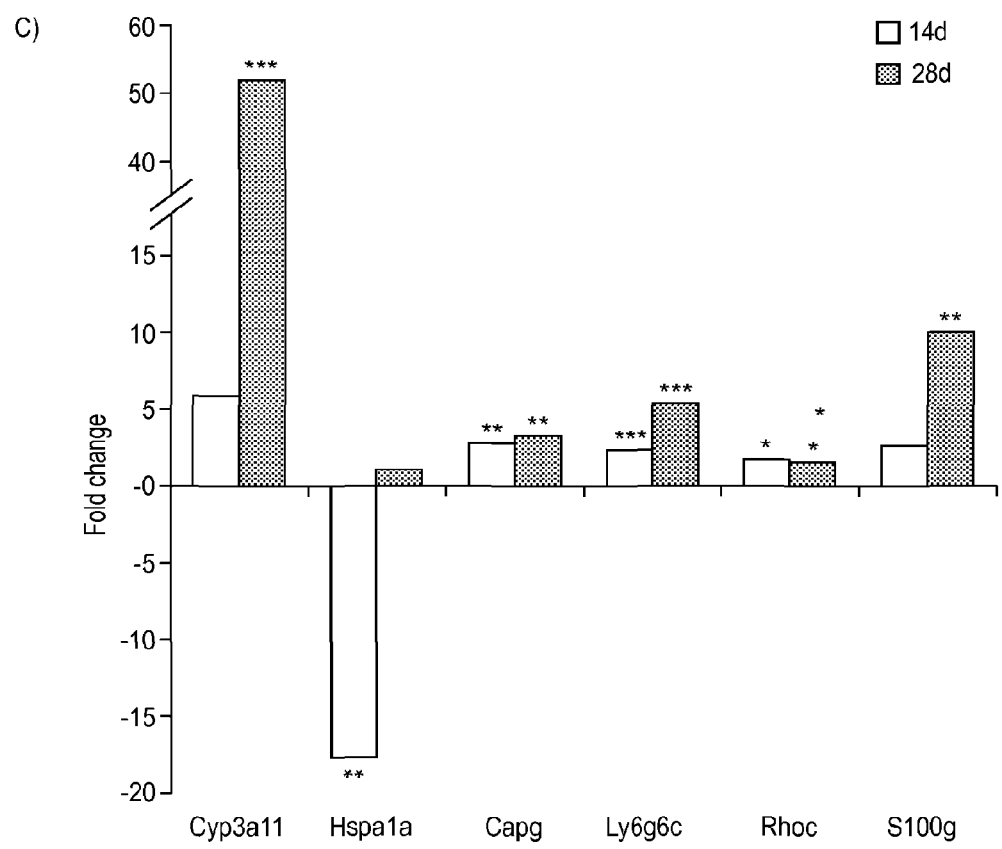

To further investigate the effects of host-adaptation on the *R. hominis* transcriptome, in vitro stimulation of human intestinal epithelial cells (Cato-2 and HT-29) was performed. This showed that the conjugation/mobilization transfer gene mobA/mobL protein1, which was induced by adaptation to the mouse gut, was also increased in both cell lines (FIG. 3F). Consistent with the in vivo data, the flagellin gene MotA was upregulated in Caco-2 cells. Genes involved in butyrate metabolism showed differences between the two cell lines, with downregulation seen in Caco-2 cells and upregulation in HT-29 cells. *R. hominis* Affects T Cell Pathways Mostly in the Colon The colonization of GF mice with *R. hominis* correlated with increased gut gene expression which was highest in the colon. (FIG. 4A). Differential expression was most profound at 28 d after colonization, with 159 genes up-regulated and 143 genes down-regulated. The number of differentially expressed genes in the ileum at 14 d was similar to the ascending colon, with 79 genes up-regulated and 119 genes down-regulated. Differential expression in the ileum was very low at 28 d, consistent with reduced colonization levels. The transcriptomic response differed at the two time-points, as shown by the clear separation of significant transcripts by heatmap analysis (FIG. 4B). Positive Real-time PCR validation of Affymetrix data is shown in FIG. 4C.

The majority of pathways affected at 14 d in the ileum and the ascending colon grouped into the categories cell differentiation, cell cycle regulation and tissue remodeling.

Importantly, immune response was the major pathway group induced at 28 d in the ascending colon. The 36 significantly affected pathways in this category were mostly involved in T cell function and included the IL-10 signaling pathway, the ICOS pathway in T-helper cell and regulation of T cell function by CTLA-4. The genes involved in these pathways showed both up-regulation and down-regulation, so while these pathways were significantly affected by the presence of *R. hominis*, the precise net functional effects on T cell differentiation requires further investigation. However, enhanced IL-10, CD3s and IL-13 and changed expression of IFN-γ was confirmed by Real-time PCR (FIG. 7), suggesting that *R. hominis* colonization may favor Treg and Th2 cell differentiation pathways. Gene Ontology analysis was applied to obtain additional information on the functional classification of differentially regulated genes. The GO-process for 'actin polymerization' (G0:0030041) (Arpc3, Capg, Cdc42ep5 and Rhoc) was up-regulated at 28 d in the colon in *R. hominis* colonized mice (FIG. 8). Actin polymerization at the immune synapse is required for T cell activation and effector function. Gene induction was further confirmed by Real-time PCR (FIG. 4C). Overall, this data indicates that *R. hominis* actively effects the adaptive immune response in the colon by positively influencing T cell regulation.

Related to these results was the induction of members of the Ly6 family in the ascending colon. In particular, the GPI-anchored gene product of Ly6g6c was up-regulated 25-fold, and the related gene Ly6g6e was up-regulated twofold at 28 d. Most hematopoietic cells express one or more members of the Ly6 family including neutrophils and plasmacytoid dendritic cells. Furthermore, a possible role of Ly6 in T cell activation, differentiation and maturation has been proposed (15).

Figure 5:
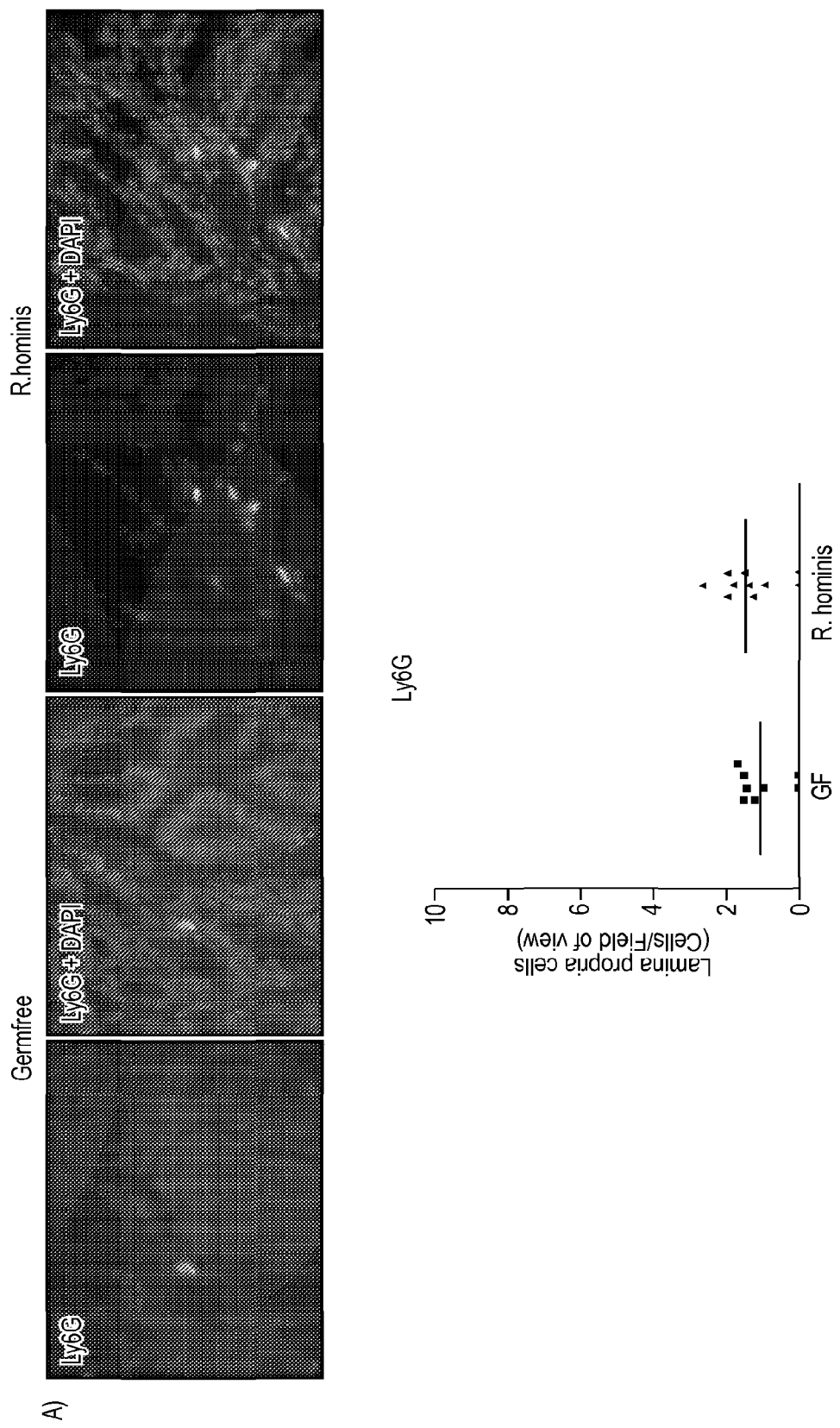
FIG. 5 shows expression and localization of T cell markers in colon. Immunofluorescence and analysis of lamina propria cells labeled with anti-Ly6G (A), anti-CD3 (B) and anti-CD11b (C) in lamina propria of GF mice and *R. hominis*-treated mice. *P<0.05.
Figure 5:
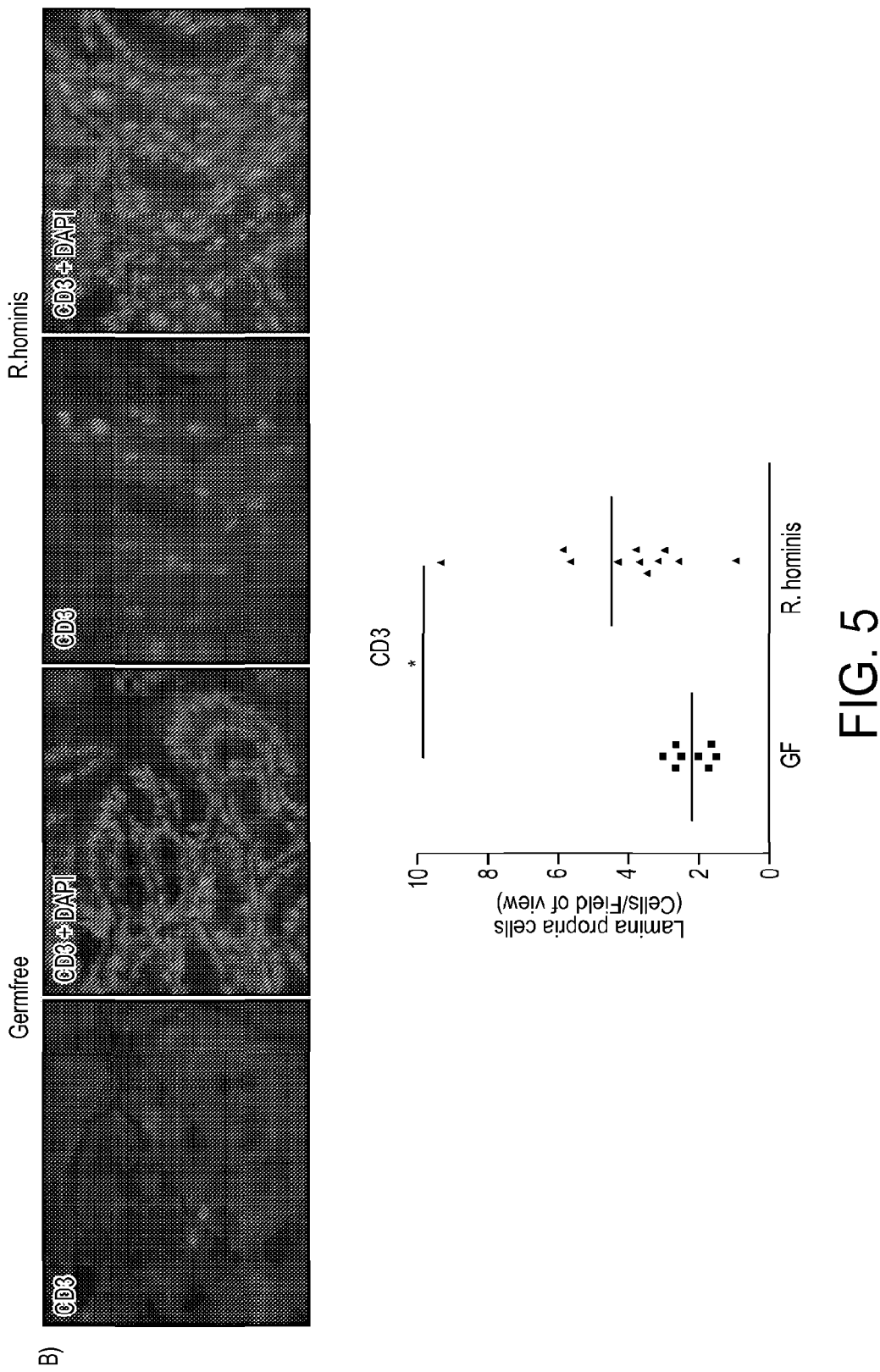
Figure 5:
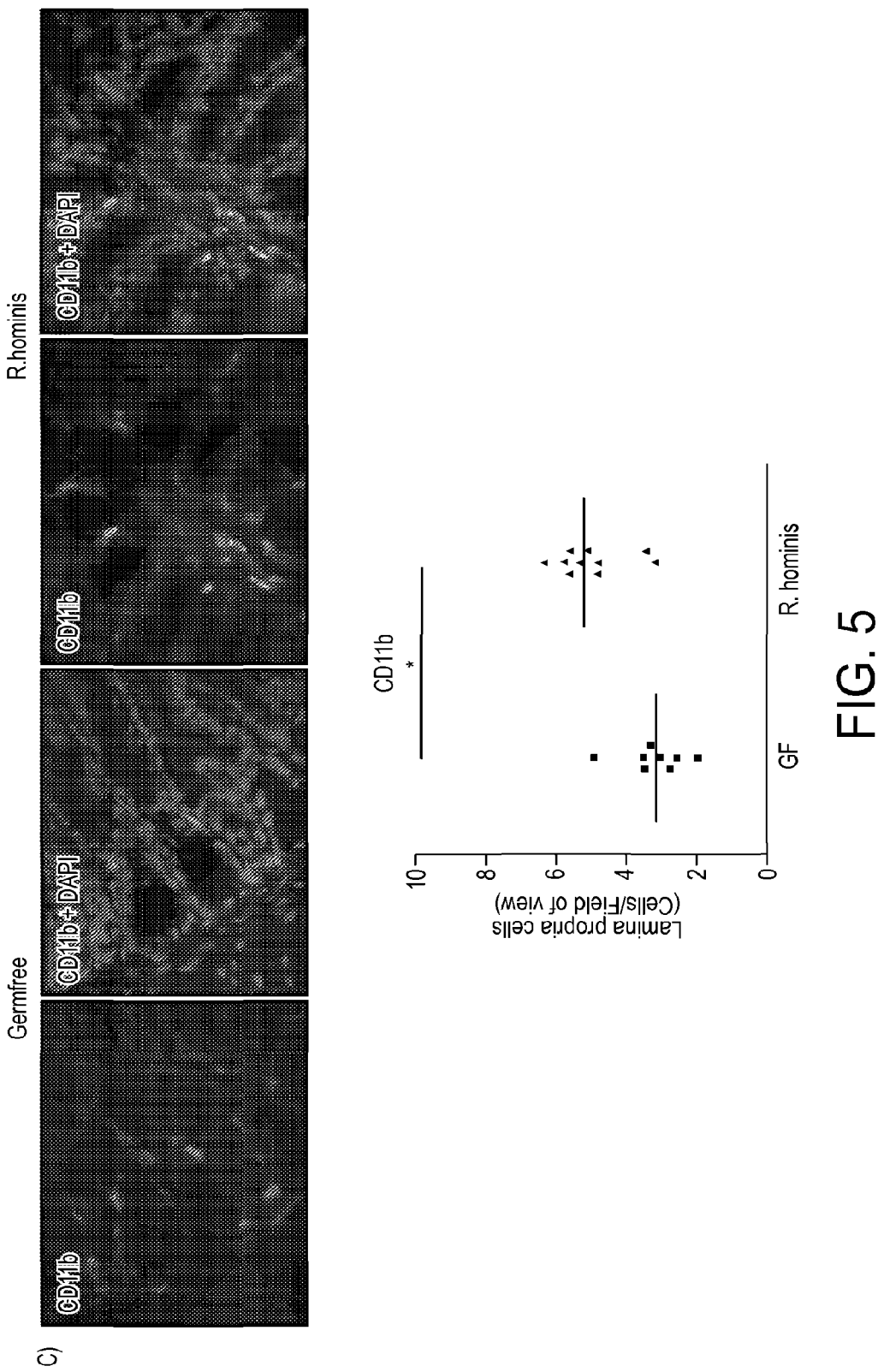
Figure 5:
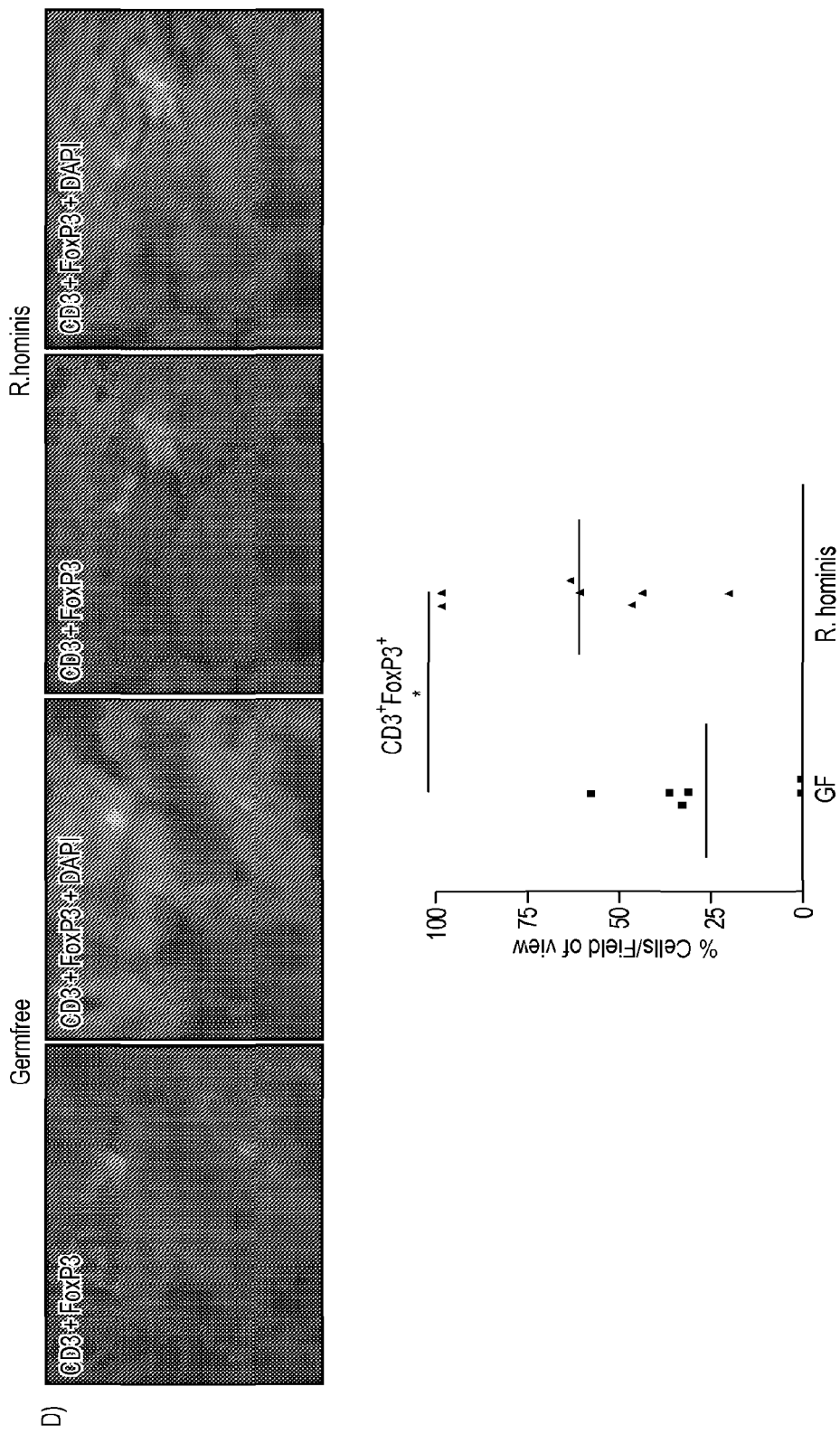

Immunocytochemistry confirmed increased presence of Ly6G+, CD11b+ and CD3+ cells in *R. hominis*-colonized mice (FIG. 5). Consistent with the data showing T cell pathways mainly dominated by Treg responses, was a statistically significant increase in double-positive CD3+ FoxP3+ T cells in the colon of *R. hominis*-inoculated mice. Clearly colonization of *R. hominis*, as a single bacterial species, induced a significant increase in a population of CD3+ FoxP3+ cells, particularly in the colon of these mice. *R. hominis* Modulates Innate Immune Response Genes in Both the Ileum and Colon and Attenuates Colitis in IL 10KO Mice Genes involved in innate immunity and gut barrier function were significantly induced by the presence of *R. hominis* in the ascending colon. The GO-process 'innate immune response' (G0:0045087) was up-regulated and included the TLR-related genes Tlr5, Tlr1 and Vnn1. The up-regulation of Tlr5 was interesting, particularly given the corresponding induction of flagellar genes and the presence of flagellin protein in *R. hominis* during gut colonization, and may infer a role for this innate signaling pathway in mediating other innate and adaptive immune responses. The coupling between TLR5 signaling and CD4+ T cell responses has recently been demonstrated for flagellate pathogens (16). Similarly, the role of TLR2 in facilitating the colonization of *Bacteroides fragilis*, Treg propagation and immune homeostasis has been shown (17).

Other innate immune genes affected in the colon by *R. hominis* included the antimicrobial peptides Defb37, Pla2g3, Muc16 and Itln and the gut barrier function genes Sprrla, Cldn4, Pmp22, Crb3 and Magi3. Innate immune genes showing up-regulation in the ileum in response to *R. hominis* included Defcr20, Pcgf2, Ltbp4, Igsf8 and Tcfe2a. Interestingly, Pcgf2 negatively regulates the expression of different cytokines, chemokines, and chemokine receptors and may play an important role in controlling inflammatory responses in gut tissues in response to this commensal bacterium. Interestingly, we also showed negative regulation of the NF-KB pathway (G0:0043124) by *R. hominis*, which, like *B. thetaiotaomicron* (19), may contribute to immune homeostasis by down-regulating this inflammatory cascade.

Figure 6:
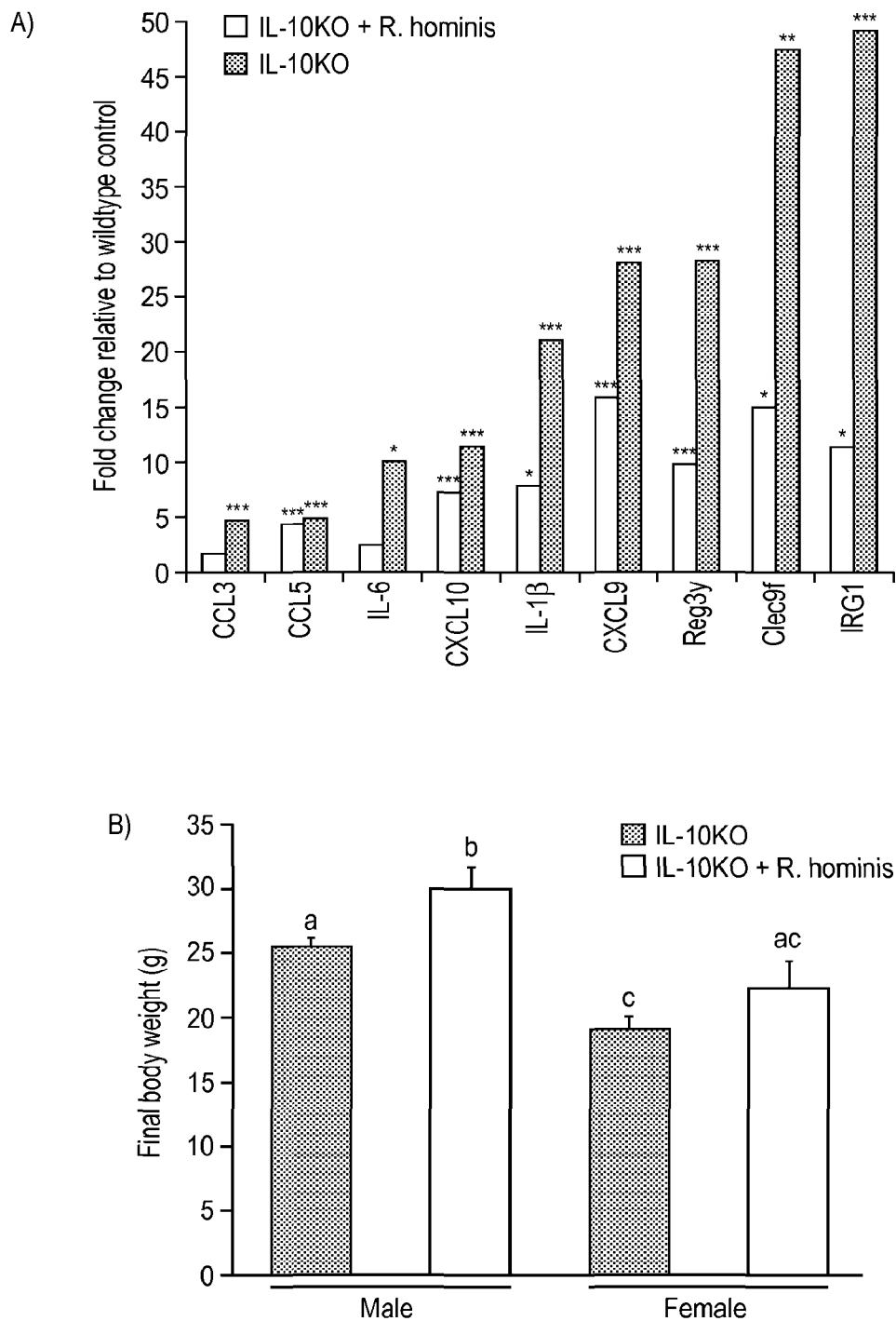
FIG. 6 shows the anti-inflammatory effects of *R. hominis* in an experimental model of colitis. IL-10KO mice were dosed three times a week for 14 weeks. (A) Untreated IL-10KO mice had strong elevation of all genes compared to wild-type mice, while differential gene expression was lower in *R. hominis*-treated animals. Real-time PCR results are means of triplicates, *P<0.05, P<0.01, *P<0.001. (B) Bodyweights of untreated IL-10KO and *R. hominis*-treated IL-10KO animals at the end of the study. (C)
Figure 6:
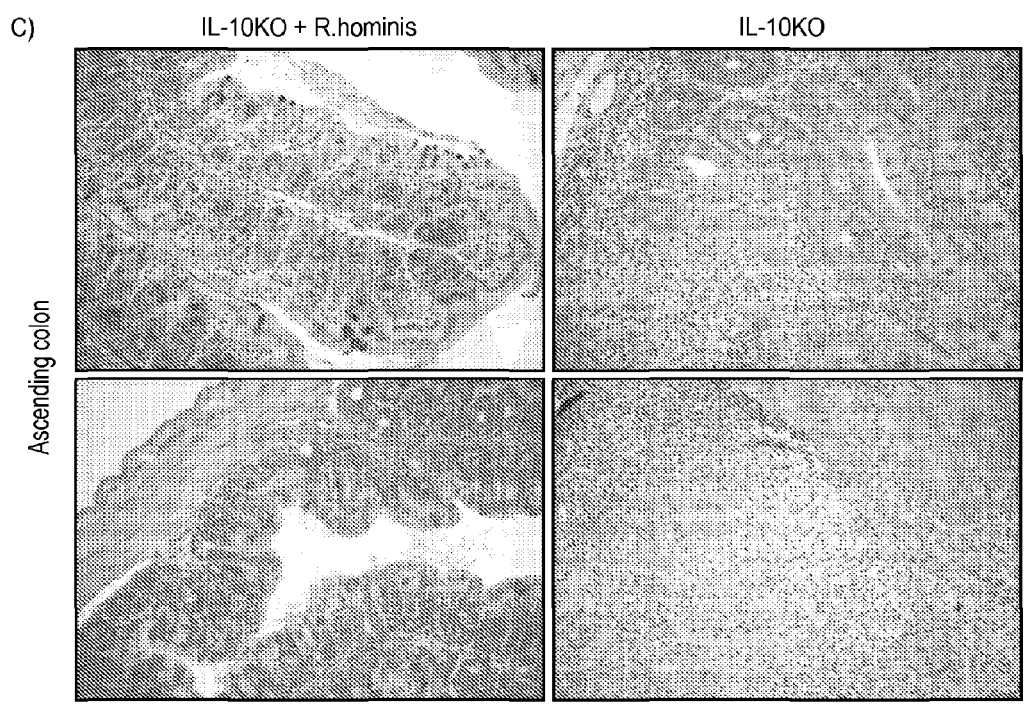

The IL-10 knockout mouse model was used to test the therapeutic efficacy of *R. hominis*, due to the control of inflammatory pathways as well as the positive effects on Treg induction in mono-associated mice. Mice were dosed (~50 µl, $10^{10}$ CFU) three times a week from weaning at 20 d of age for a period of 14 weeks. Gene expression of a panel of pro-inflammatory biomarkers showed that untreated IL-10KO mice had strong elevation of all investigated genes compared to wild-type mice, with gene induction ranging from 4- to 49-fold (FIG. 6A). Pro-inflammatory gene induction was significantly lower in *R. hominis*-treated compared to untreated mice, indicating strong therapeutic benefits of oral administration of *R. hominis*. Bodyweights of *R. hominis*-treated animals were also heavier at the end of the study compared to untreated animals, and this effect was statistically significant in males (FIG. 6B). Finally, histological analysis showed the presence of severe inflammation in the ascending colon of untreated IL-10KO, while *R. hominis*-treated animals had a relatively healthy-looking colonic mucosa. *R. hominis* Colonization Influences Satiety Genes and Body Composition Significant metabolic actions of *R. hominis* in mono-associated mice were also evident. The GO-processes 'negative regulation of response to food' (GO:0032096), 'negative regulation of appetite' (GO:0032099), and 'regulation of catecholamine secretion' (GO:0050433) were all down-regulated in the ascending colon after colonization with *R. hominis*. This data infers that *R. hominis* exerts a stimulatory effect on host appetite. The genes involved in these processes were Agt, Cartpt, Cck and Cxcl12, with fold changes ranging from 2- to 12-fold. Cck, in particular, plays a major role in digestion and satiety as a hunger suppressant. Gcg also showed down-regulation at this gut site.

To establish whether these gene changes had physiological relevance in relation to food intake and body composition, dry carcass weight and composition analyses were performed. Interestingly, the dry carcass weights of *R. hominis*-associated mice were significantly heavier compared to GF animals, and the differences were most discernable at 14 d. Further carcass lipid analysis showed that total adiposity was also significantly higher in *R. hominis*-treated animals at 14 d. These finding are consistent with recent data revealing the role of Firmicutes in energy harvest through dietary fermentation, but also support the notion that gut bacteria can in fact modulate the brain-gut axis and appetite-regulating hormones. Discussion The long-term co-evolution of host-microbe mutualism has likely driven the selection of functionally important bacterial species in the gut, the majority of which are not highly represented in other ecosystems. Currently, there is limited information regarding the contribution of individual members of the microbial community to intestinal functions, particularly in relation to development of the mucosal immune system.

Recent work using a reversible colonization model based on *E. coli* (HA 107) has demonstrated that live bacteria are required in numbers approaching 108 CFU s per gram of content for the immune-inducing effects on IgA (20). Recently, the specific functions of SFB and *Bacteroides fragilis* have been investigated in the mouse gut to define their individual contributions to T cell biology and both these bacteria have been shown to be potent inducers of Tregs and Th17 cells (5, 8, 9). The effects of individual members of the cluster XIVa Firmicutes have not been reported previously, although their presence in the ASF, which also affects T cell differentiation has been noted (10).

The applicant has demonstrated herein the first successful mono-association of the germ-free mouse gut with an anaerobic bacterium, *R. hominis*, which is a member of the Firmicutes phylum. The extreme oxygen sensitivity of bacteria like *Roseburia* requires strict anaerobic culture techniques, making it difficult to perform functional characterization. The applicant established stable mono-colonization of *R. hominis* in germfree mice and produced the complete annotated genomic sequence to uncover its metabolic organization, physiology, and symbiotic properties. It was found that the transcriptional responses of *R. hominis* following colonization could be attributed to both the host gut environment and diet. The host-driven effects dominated the response of *R. hominis* following mono-association. These included gene transfer, membrane transport, chemotaxis and motility subsystems. The strong up-regulation of genes involved in mobilization transfer supports the view that the gut environment is highly conducive to horizontal gene exchange between members of the gut microbiota. Thus, this environment may accelerate the dissemination of genes important for bacterial survival, colonization and function within the gut ecosystem.

The role of motility and flagellar apparatus in host colonization is well-elaborated for pathogenic bacteria but much less is known about the role of flagellar proteins in commensal bacteria. In vivo experiments revealed a stimulatory effect of the host intestinal environment on the expression of flagellin genes. Flagellin signals are perceived by host TLR5 receptors (24) and many pathogenic flagellin structures induce strong pro-inflammatory responses (24). Signaling through TLR5 in response to by resident flagellated commensals may be important for homeostasis, since deletion of TLR5 results in spontaneous colitis in mice (25). The enhanced expression of *R. hominis* flagellin in vivo is therefore of potential interest. Other work has shown that *E. coli* flagellin mutants have a colonization advantage over wildtype flagellated strains, possibly due to absence of innate recognition by TLR5 signaling (26, 27). The applicant has shown that for certain Firmicutes, upregulation of flagellin is a natural response to gut colonization. *R. hominis* flagellin protein remains expressed in vivo and correlates with sustained colonization, absence of overt inflammation and expansion of T cells of regulatory phenotype. Hence, commensal flagellin structures through TLR5 may help direct immune tolerance responses. Additional data based on TLR5KO and flagellin mutants of *R. hominis* will further clarify the importance of commensal flagellins in relation to immune homeostasis but the observed protective effect of *R. hominis* in IL-1 0 KO mice supports this hypothesis, although other signaling moieties such as butyrate may also contribute to immune regulation.

A clear role was established for *R. hominis* in promoting gut barrier function and innate immunity in the mouse colon. Tight junctions, gap junctions and adherens junctions operate to limit bacterial translocation to the subepithelial layer (28). Both Crohn's disease and ulcerative colitis are characterized by loss of barrier function and tight junction integrity. Interestingly, dysbiosis of the gut microbiota in IBD is associated with a reduction in Firmicutes (1, 29). The observation that *R. hominis* actively enhances the expression of barrier genes suggests that their loss in IBD patients may be functionally significant. Activation of tight junction complexes is not just the prerogative of *R. hominis*; other commensals, such as *Bacteroides thetaiotaomicron* and *Lactobacillus acidophilus*, also enhance mucosal barrier function (18, 30), inferring probiotic opportunities with these bacteria in human IBD.

The effects of *R. hominis* on the gut immune system were intriguing. The strongest effects were noted in the ascending colon and genes such as Ly6g6c were strongly up-regulated, as well as pathways involved in T cell regulation and differentiation and actin polymerization at the immune synapse, which are implicated in T cell activation and effector functions. Although the expression of Treg genes in response to *R. hominis* colonization was not very strong, the most affected T cell pathways included those related to IL-1 0, ICOS and CTLA-4, which are all involved in supporting Treg differentiation. Importantly, the applicant was able to demonstrate significant increases in CD3+FoxP3+ cells in the colons of these mice. These findings complement the recent data on other *Clostridium* species that drive Treg differentiation. Clearly, *R. hominis* can promote mucosal T cell expansion and impacts on T cell differentiation.

It was interesting to note the strong immune effects in the colon compared to the ileum, especially at 28 d after mono-colonization with *R. hominis*. The transcriptomic data at 14 d suggests that some immune priming could be initiated in ileum at this time-point. The effects on the different T cell subsets in the ascending colon at 28 d may thus reflect a trafficking and homing of cells from ileum to mesenteric lymph node to the colon.

An interesting additional biological effect of *R. hominis* colonization was the regulation of genes influencing responses to food and control of appetite. In particular, the satiety hormones Cck and Gcg were significantly reduced. The effects of Cck on food intake are mediated via a vagal afferent pathway. This is the major neural pathway by which information about ingested nutrients reaches the central nervous system to influence both gut function and feeding behavior. Cck acts on the vagal system to decrease expression of molecules that stimulate appetite and feeding, and to increase expression of molecules that inhibit feeding and decrease appetite (Npy2r and Cartpt, both down-regulated two-fold in the current study). No link between Cck, Gcg and commensal bacteria has been reported thus far, however, both fatty acids and proteins are potent inducers of Cck and Gcg (31). *R. hominis* produces short-chain fatty acids such as butyrate with aliphatic tails of less than six carbons; this metabolic activity has been reported to reduce the stimulatory effect on plasma Cck observed with longer chain fatty acids (32). Interestingly, carcass weight analysis revealed that both body weight and lipid content was indeed significantly increased with *R. hominis*, consistent with body weight increases observed in conventionalization of germ-free mice (33). Whether this is a direct effect of a reduction in satiety hormones as seen in the current study remains to be seen, as the involvement of Cck and Gcg has not been reported previously. However, it is important to acknowledge that a link between microbiota colonization and energy harvest from the diet, in part through release of SCFAs, has been shown previously (34). Given that *R. hominis* is a major butyrate producer, this mechanism is likely also to contribute to the metabolic efficiency observed following *R. hominis* treatment.

In summary, mono-association of the murine gut with *R. hominis* induced strong bi-directional gene expression events consistent with changes in bacterial membrane transport, chemotaxis and motility of this gut-adapted bacterium and a concomitant activation of the innate and adaptive immune system of the host. This metabolically active bacterium also exerted important effects on appetite and satiety genes which correlated with enhanced body weight gain in colonized mice. Compositions Another aspect of the invention relates to a composition comprising a bacterial species as described above and a pharmaceutically acceptable excipient, carrier or diluent. Suitable excipients, diluents, carriers are described below.

The composition may be any composition, but is preferably a composition to be administered orally, enterally or rectally. For example, the composition may be an edible composition. "Edible" means a material that is approved for human or animal consumption.

Another aspect of the invention relates to a probiotic composition comprising a bacterial species as described above.

As used herein, the term "probiotic" means microbial cell preparations or components of microbial cells with a beneficial effect on the health or well-being of the host. (Salminen S, Ouwehand A. Benno Y. et al "Probiotics: how should they be defined" Trends Food Sci. Techno. 1999:10 107-10).

Preferably, the probiotic composition is an orally administrable composition of metabolically active, i.e., live and/or or lyophilized, or non-viable heat-killed, irradiated or lysed probiotic bacteria. The probiotic composition may contain other ingredients. The probiotic composition of the invention can be administered orally, i.e., in the form of a tablet, capsule or powder. Encapsulated products are favoured for *R. hominis* as it is an anaerobe. Other ingredients (such as vitamin C, for example), may be included as oxygen scavengers. Prebiotic substrates such as these improve the colonisation and survival in vivo. Alternatively, the probiotic composition of the invention may be administered orally as a food or nutritional product, such as milk or whey based fermented dairy product, or as a pharmaceutical product.

A suitable daily dose of the probiotic bacteria is from about $1 \times 10^3$ to about $1 \times 10^{11}$ colony forming units (CFU), more preferably from about $1 \times 10^7$ to about $1 \times 10^{10}$ CFU, more preferably, about $1 \times 10^6$ to about $1 \times 10^{10}$ CFU.

In one preferred embodiment, the composition contains the bacterial species and/or cellular components thereof, as active ingredients, in an amount of from about $1 \times 10^6$ to about $1 \times 10^{11}$ CFU/g, respect to the weight of the composition, preferably from about $1 \times 10^8$ to about $1 \times 10^{10}$ CFU/g. The dose may be of 1 g, 3 g, 5 g, and 10 g.

Typically, a probiotic is optionally combined with at least one suitable prebiotic compound. A pre biotic is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

Preferably, the composition of the present invention includes a pre biotic in an amount of from about 1 to about 30% by weight, respect to the total weight composition, preferably from 5 to 20% by weight. Preferred carbohydrates are selected from: fructo-oligosaccharides (or FOS), short-chain fructo-oligosaccharides, inulin, isomalt-oligosaccharides, pectins, xylooligosaccharides (or XOS), chitosan-oligosaccharides (or COS), beta-glucans, arable gum modified and resistant starches, polydextrose, D-tagatose, acacia fibers, carob, oats, and citrus fibers. Particularly preferred prebiotics are the short-chain fructo-oligosaccharides (for simplicity shown hereinbelow as FOSs-c.c); said FOSs-c.c. are not digestible carbohydrates, generally obtained by the conversion of the beet sugar and including a saccharose molecule to which three glucose molecules are bonded. Feedstuffs/Products A further aspect of the invention relates to food products, dietary supplements, nutraceuticals, nutritional formulae, drinks and medicaments containing a bacterial species as defined above, and use thereof.

In one preferred embodiment, the composition comprises additionally at least one other kind of other food grade bacterium, wherein the food grade bacterium is preferably selected from the group consisting of lactic acid bacteria, bifidobacteria, propionibacteria or mixtures thereof.

One aspect of the invention relates to a food product comprising the bacterial species defined above. The term "food product" is intended to cover all consumable products that can be solid, jellied or liquid. Suitable food products may include, for example, functional food products, food compositions, pet food, livestock feed, health foods, feedstuffs and the like. In one preferred embodiment, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present invention include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

In one preferred embodiment the composition according to the present invention is a food product intended for humans, pets or livestock. The composition may be intended for animals selected from the group consisting of dogs, cats, pigs, cattle, horses, goats, sheep or poultry. In a preferred embodiment, the composition is a food product intended for adult species, in particular human adults.

In the present invention, "milk-based product" means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

One aspect of the invention relates to a feedstuff or animal feed comprising the bacterial species defined above.

The compositions of the present invention may be—or may be added to—food supplements, also referred to herein as dietary or nutritional supplements or food additives. Thus, another aspect of the invention relates to a dietary supplement or food additive comprising one or more bacterial strains according to the invention.

The bacterial species and probiotic compositions according to the invention may also be used in animal nutrition (e.g. in pig nutrition), particularly in the early-weaned period and growing fattening period. The probiotics are expected to enhance immune function reduce and prevent infectious diseases, beneficially alter the microbiota composition, and improve growth and performance of animals, for example, through increased feed conversion efficiency.

Diluents, Excipients and Carriers

As mentioned above, the invention also relates to compositions, more preferably pharmaceutical compositions or nutritional supplements, comprising the bacterial species defined above, and use thereof. The bacterial species is generally administered in admixture with a pharmaceutically or nutritionally acceptable carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption and that are used as standard in the food industry. Typical nutritionally acceptable carriers, diluents and excipients will be familiar to the skilled person in the art.

Administration

The compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. Preferably, the compositions of the present invention are adapted for oral, rectal, vaginal, parenteral, nasal, buccal or sublingual routes of administration.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The bacterial strain can also be incorporated into an ointment consisting of a white wax or white soft paraffin base together with such stabilisers and preservatives as may be required.

Compositions may be formulated in unit dosage form, i.e., in the form of discrete portions containing a unit dose, or a multiple or sub-unit of a unit dose. Dosage A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific bacterial strain employed, the metabolic stability and length of action of that strain, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The usual effective daily dose in humans is from about $1\times10^3$ to about $1\times10^{11}$, more preferably, from about $1\times10^7$ to about $1\times10^{11}$, even more preferably, from about $1\times10^6$ to about $1\times10^{10}$ CFU. Combinations In a particularly preferred embodiment, the compositions of the invention are administered in combination with one or more other active agents. In such cases, the compositions of the invention may be administered consecutively, simultaneously or sequentially with the one or more other active agents.

The present invention is further described by way of the following non-limiting examples. Examples Materials and Methods Bacterial Growth Conditions R. hominis A2-183T(=DSM 16839T=NCIMB 14029T) was grown anaerobically on synthetic YCFA or complex M2GSC media. Culture was inoculated from frozen stock into Hungate tubes and incubated overnight at 37° C. Bacteria were then grown on M2GSC agar plates for 48 h in a MACS-MG-1 000 anaerobic workstation (Don Whitley Scientific) under 80% N2, 10% C02, and 10% H2 at 37° C. The effect of mucin was investigated by adding 0.5% (w/v) mucin from porcine stomach type III (Sigma-Aldrich) to the YCFA medium.

For colonization of germfree mice, R. hominis was grown in YCFA media overnight at 37° C. The culture was spun down and the pellet was resuspended in one mL of YCFA media, supplemented with 2% cysteine (w/v, SigmaAldrich) and 3% ascorbic acid (w/v, Sigma-Aldrich).

Animal Experiments

Germ-free animal experiments were performed in the INRA gnotobiotic rodent breeding facility at Jouy-en-Josas (ANAXEM plateform, Institut Micalis, INRA, Jouy-en-Josas, France). All animal experiments were approved by the local ethical committee. Eighteen germfree C3H/HeN male mice were allocated into control (N=8) and treatment (N=10) groups and caged individually in plastic isolators. The mice were fed ad libitum on a sterilized commercial diet (R03-40; UAR). At day 0, animals in the treatment group were given 100 μL of R. hominis culture by gavage, while control animals were given 100 μL YCFA media. At day 14 and 28, four control animals and five R. hominis-treated animals were sacrificed. C57/BL6 IL-10KO experiments were performed at the Rowett Institute of Nutrition and Health (Aberdeen, Scotland, UK). Wild-type mice (N=8), IL-10KO (N=12) and IL-10KO+R. hominis (N=11) were analysed 14 weeks from the outset of the experiment. Briefly R. hominis was administered 3 times per week at $10^9$ cfu/day.

The ileum, ascending colon and descending colon were divided into four equal parts and transferred to RNAlater (Ambion), neutral buffered formalin (Sigma-Aldrich) or liquid nitrogen. The whole caecum and transverse colon were transferred to RNAlater. Histopathology was also evaluated in the IL-10KO mice.

Tissue Culture Experiments

All cell culture reagents, unless specified otherwise, were supplied by Sigma-Aldrich. $2\times10^5$ Caco-2 or HT29 cells in 1.5 mL DMEM (high glucose, HEPES) medium supplemented with heat-inactivated fetal bovine serum (Gibco), penicillin, streptomycin, amphotericin B and L-glutamine were seeded into the upper compartments of a six-well transwell plate (Corning). The lower compartments contained 3.0 mL of the same medium. Cells were incubated at 37° C. in a 5% C02 atmosphere until 3 days post-confluence, washed with Hanks' solution to remove antibiotics and FCS and stepped down in DMEM supplemented with L-glutamine, sodium selenite and transferrin for 24 h without antibiotics. Transwell inserts were then transferred to an anaerobic culture box within the anaerobic workstation at 37° C. The upper compartment of each insert was filled with anaerobic DMEM cell medium, while the lower compartment was filled with oxygenated DMEM.

R. hominis A2-183 culture was harvested at exponential phase by centrifugation at 3,500×g for 5 min. The pellet was washed and resuspended in 0.8 mL anaerobic DMEM. One hundred microliters of bacterial suspension ($10^8$ CFU/mL) was added to experimental wells. The control wells received the same amount of medium without bacterial cells. Additional control included bacterial cells incubated without Caco-2 or HT29 cells.

Bacterial and eukaryotic cells were harvested after 2 h and 4 h incubation. Both non-adherent and adherent bacteria were aspirated and stored in RNAlater. The viability of R. hominis cells was tested by plating onto YCFA plates. Caco-2 cells or HT-29 cells were harvested from the wells and also stored in RNAlater. R. hominis Library Construction R. hominis chromosomal DNA for small-size library construction and pyrosequencing was isolated using an UltraClean™ Microbial DNA Isolation Kit (Mo Bio Laboratories Inc) and high-molecular-weight DNA for fosmid libraries was isolated using a Wizard Genomic DNA Purification kit (Promega). DNA integrity was checked by gel electrophoresis.

DNA was mechanically sheared using a Nebulizer kit (Invitrogen) and fractionated by gel electrophoresis. DNA fragments of desired size were excised from the gel and purified using a Wizard® SV Gel and PCR Clean-Up System (Promega). End-repair was done with a DNA Terminator End Repair Kit (Lucigen). 1.5-3.5 kb fragments were cloned using the CloneSmart® LCAmp kit (Lucigen) and a 4-8 kb library was constructed using the pJAZZ®-OC vector (Lucigen). Fosmid libraries were constructed using the CopyControl™ Fosmid Library Production Kit (Epicentre Biotechnologies). Colonies were picked using an automated colony picker (BioRobotics BioPick, Genomic Solutions) and archived into 384-well microtitre plates containing 70 μL 2×LB medium supplemented with 10% glycerol and corresponding antibiotic. Cells were grown overnight at 37° C. with shaking and stored at −80° C.

Sequencing, Assembly, and Annotation

Templates for sequencing of small-size libraries were generated by PCR using one μL of clone biomass and primers SL1 and SR2 surrounding the cloning site of pSMART-LCAmp. PCR products were purified using Multiscreen PCR Clean-up filter plates (Millipore). Recombinant DNA from the pJAZZ®-OC clones was isolated using the Wizard® SV 96 Plasmid DNA Purification System (Promega). Fosmid DNA was isolated using the Fosmid-MAX™ DNA Purification Kit (Epicentre). End-reads of DNA fragments from R. hominis WGS libraries with different insert sizes were obtained using CEQ8000 (Beckman Coulter) and ABI 3770 (Applied Biosystems) DNA sequencers. Genomic DNA from R. hominis was also sequenced using 454 GS20 (454 Life Sciences) and 454 FLX sequencers (Roche). The Sanger and 454 data were assembled with MIRA version 3 (http://chevreux.org/projects_mira.html; (35). The RAST annotation pipeline (http://rast.umpdr.org; (36)) was used for automatic and manual annotation of the genome and for comparative genomic analyses. The annotated genomic sequence of *R. hominis* A2-183 was submitted to GenBank under the accession number CP003040.

Microarray Analyses Bacterial Microarray

Bacterial RNA was isolated from mouse caecum contents using the RNeasy mini kit, and further processed with the MICROBEnrich™ kit (Ambion), the MICROBExpress™ bacterial mRNA enrichment kit (Ambion), and the MessageAmp™ II-bacteria RNA amplification kit (Applied Biosystems). RNA was labeled with either dCTP-Cy3 or dCTP-Cy5 during eDNA synthesis (CyScribe First strand eDNA labelling kit; Amersham). Labeled products were purified using the CyScribe GFX purification kit (Amersham). PCR products amplified from 6000 clones in the RA8 library were arrayed in duplicate on amino silane-coated microscope slides (Coming) using a MicroGrid II TAS (BioRobotics). Amplified fragments of the housekeeping genes rpoD and gyrA were randomly distributed on the array as controls. Microarray hybridization was performed in the GeneTAC hybridization station (Genomic Solutions). Dye labeling was swapped for a second hybridization, and a separate RNA purification was also labeled and hybridized twice, to ensure reproducibility and to obtain statistically significant results. In total, four slides were hybridized for each comparison, for a total of 12 hybridizing spots per amplified clone. Fluorescence was measured in two channels using a GeneTAC LS IV (Genomic Solutions) with GeneTac Integrator version 3.0.1 software. Spot intensities were log-transformed and Loess normalization was applied to remove differences in probe labelling and hybridization efficiencies. One-sample t-tests were used on the log-ratio values to test for differential expression. Data was considered significant when fold change>2 and P<0.05. Mouse Microarray Analysis Ileum and ascending colon tissue was removed from RNAlater and lyzed in Trizol (Invitrogen). RNA was isolated using standard chloroform/isopropanol steps. Total RNA was further purified with the RNeasy kit (Qiagen), including an RNase-free DNase I (Qiagen) digestion step. RNA integrity was determined using the Agilent 2100 Bioanalyzer (Agilent Technologies). Total RNA was processed into biotin-labeled cRNA using the One-Cycle Target Labeling Kit (Affymetrix). Hybridization to the GeneChip Mouse Genome Array (Affymetrix) on a GeneChip Fluidics Station 450 (Affymetrix) was performed at the Institute of Medical Sciences Microarray Core Facility (University of Aberdeen, UK). Chips were scanned with an Affymetrix GeneChip Scanner 3000 (Affymetrix). Image quality analysis was performed using Gene Chip Operating Software (GCOS) (Affymetrix). Further data analysis was performed with the freely available software packages R (http://www.r-project.org) and Bioconductor (http://www.bioconductor.orq). The moderated F-test provided by the Bioconductor package limma was used to test for differential expression. Data was considered significant when P<0.05 using the Benjamini and Hochberg false discovery method. Statistical analysis was performed separately for each of the two time-points. All differentially expressed genes (P<0.05) were imported into Meta Core analytical software (GeneGo, St Joseph, Mich.) to generate pathway maps. Integrated pathway enrichment analysis was performed using the knowledge-based canonical pathways and endogenous metabolic pathways. Ranking of relevant integrated pathways was based on p-values calculated using hypergeometric distribution. P-values represented the probability of a given number of genes from the input list to match a certain number of genes in the map by chance, considering the numbers of genes in the experiment versus the number of genes in the map within the full set of all genes on maps. Gene Ontology (GO) based functional interpretation of the data was performed using DAVID (http://david.abcc.ncifcr-f.gov), an expanded version of the original web-accessible program (37). Significantly different transcripts (P<0.05) were allocated into the GO category 'Biological Process' to unearth patterns of gene expression significantly enriched for specific GO terms.

Microarray data were submitted to the National Center for Biotechnology Information (NCBI) Gene Expression Omnibus (accession number GSE25544; http://wvvw.ncbi.nlm.nih.gov/geo). RT-PCR Analysis Bacterial PCR primers were designed using the online tool Primer3Plus (38) and purchased from Sigma-Aldrich. Real-time PCR analysis was performed using a 7500 Fast Real-Time PCR System (Applied Biosystems) with the Power SYBR Green PCR Master Mix (Applied Biosystems). PCR was performed as follows: one cycle at 95° C. for 10 min, followed by 40 cycles at 95° C. for 15 sec and 60° C. for 1 min, ending with a dissociation step. All samples were run in triplicate. GyrA was used as a reference gene for normalization due to its low variation between samples.

For host gene expression, 2 fig of total eukaryotic RNA isolated from the ileum and ascending colon was reverse-transcribed into eDNA using the High Capacity eDNA Reverse Transcription Kit (Applied Biosystems) with random primers. Real-time PCR analysis was performed using a 7500 Fast Real-Time PCR System (Applied Biosystems) with the QuantiFast SYBR Green PCR Kit (Qiagen) and QuantiTect Primer Assays (Qiagen). PCR cycling conditions were as follows: one cycle at 95° C. for 5 min, followed by 40 cycles at 95° C. for 10 sand at 60° C. for 30 s, ending with a dissociation step. All samples were run in triplicate. Hprt was selected as a reference gene for normalization because of its low variation between samples. All RT-PCR data were analyzed on a logarithmic scale with base 2 by Student's t test allowing unequal variances with a significance cut-off of P<0.05. Differences were back-transformed to calculate fold changes.

Western Blot

Immuno-purified rabbit polyclonal antibodies against *Roseburia hominis* Fla2 was produced as described in Duck et al (39). In brief, New Zealand white female rabbits were immunized with synthetic peptide in complete Freund's adjuvant and boosted several times. For *R. hominis* fla2 peptide 261-275 (C-AQYNDDAKSVLEILK-COOH) and peptide 58-71 (C-GLNKASRNSQDGIS-CONH2) were used. Following immunization the antibodies were purified on an immunoaffinity column prepared by coupling the peptides to 1 mL of activated sepharose beads.

For the western blot, ascending colon gut contents were suspended in Iaemmli buffer containing 8M urea. *R. hominis* biomass (positive control) was diluted in the same buffer. Thirty μL of each sample was loaded into wells of a NuPAGE® Novex® 4-12% Bis-Tris gel (Invitrogen) and electrophoresed, followed by further processing using the WesternBreeze Chemiluminescent Immunodetection System (Invitrogen). Fla2 antibody was diluted 1:1000 in antibody diluent and incubated overnight at 4° C., followed by 1 h at room temperature with alkaline phosphatase conjugated anti-rabbit. Detection was accomplished using the Fuji LAS3000 image system. Dry Body Weight and Lipid Carcass Analysis Eviscerated mouse carcass was weighed, lyophilized to constant weight and then milled for analysis. Lipid content was determined by extraction (1:100 w/v) with chloroform/methanol (2:1 v/v) as described previously (40).

FISH Analysis

FISH analysis was performed on gut tissue sections using a general bacterial probe Eub338 and a newly designed *R. hominis* A2-183-specific probe.

Tissues fixed in neutral buffered formalin were embedded in Technovit 8100 (Heraeus Kulzer). Two-micron sections were cut using a rotary microtome (Leica/Reichert Autocut). Three sections were taken per slide at 100 μm, 200 μm and 300 μm into the tissue, resulting in nine sections per animal.

Slides were dehydrated by consecutive incubation in 50% (v/v), 80% and 96% ethanol and dried at room temperature. 16S rRNA FISH probes used were a general bacterial probe Eub338 (GCTGCCTCCCGTAGGAGT; Cy3) and a newly designed *R. hominis* A2-183-specific probe (GTACATTACATACTCTGTCAGTG; FITC), which was extensively tested for specificity against a panel of intestinal bacterial isolates. Ten microliter probe (30 ng/μL) in 100 μL hybridization buffer was applied to the dehydrated sample and incubated at probe-specific temperature. The slides were washed in washing buffer at 50° C. for 30 min, dipped in ice-cold water to remove residual washing buffer and dried under compressed air flow. Counterstaining was performed with 4',6-1.5 diamidino-2-phenylindole (DAPI; Vector Laboratories Inc) and slides were mounted with Vectashield Mounting Medium for fluorescence (Vector Laboratories Inc) to prevent fading. Bacteria were visualized using a Leica DM RBE fluorescence microscope (Leitz GMBH) and photographed with a Penguin 600CL camera (Pixera) and Viewfinder 3.0 software (Studio Lite). High-magnification images (×63) were retrieved using the Apochromatics system (Leica).

Immunofluorescence

Immuno-localization of T cell markers was examined on sequential cryosections (8 μm). Sections were fixed either in pre-cooled methanol for 30 min at −20° C. (Ly6G FITC, CD3 FITC, CD11 b FITC, all at 1:50 (BD Biosciences)), or, for the double-labeled FoxP3 (1:500, Abeam) with CD3 FITC (1:100, BD Biosciences) fixed in 1% paraformaldehyde (PFA) for 2 min at RT followed by 3 min in 0.01% Triton X in PBS. All sections were blocked with 10% BSA (Sigma) containing 10% relevant pre-immune sera in PBS (pH 7.4). Methanol-fixed tissues were incubated with primary antibodies for 1 h at RT. PFA-fixed sections were incubated with antibodies over night at 4° C. FoxP3 was visualized using Alexa goat anti rabbit 594 (1:1000, Molecular Probes). Sections were counter labeled with DAPI and mounted with Vectashield (Vector Laboratories). For quantification of positive cells, a minimum of five fields of view from each mouse section was examined, using imaging software and microscope settings described above. Histology Tissue samples were fixed for three hours in Camay's fixative (60% (v/v) ethanol, 30% (v/v) chloroform and 10% (v/v) glacial acetic acid) at room temperature with constant agitation. The samples were transferred to 70% ethanol and stored at room temperature until orientated for transverse sectioning and embedded in cold-curing resin using Technovit 8100 (Heraeus Kulzer) according to the manufacturer's instructions. The embedded tissue was mounted onto Histoblocs using Technovit 3040 (Heraeus Kulzer). Four micron sections were cut using a rotary microtome (Leics Autocut) fitted with a glass knife (TAAB Laboratories Equipment Ltd.). Tissue sections were stained using standard haemotoxylin/eosin methods and examined with a Zeiss Axioskop microscope equipped with ×10 and ×20 objectives. Images were taken using a QImaging camera and Image Pro Plus software.

Comparison of Genomes of *Roseburia*-Related Species and Strains

The Applicant produced a complete genome sequence of *R. hominis* A2-183, which is represented by a single 3,592,125-bp chromosome. Automated and manual annotation of the genome using the RAST platform revealed the presence of four ribosomal operons, 66 RNAs and 3,273 predicted proteins. The Subsystem Category Distribution for *R. hominis* A2-183, *R. inulinivorans* DSM 16841, *R. intestinalis* L1-82, *R. intestinalis* M50/1 and *Eubacterium rectale* ATCC 33656 are shown in FIGS. 11-15 respectively.

This information illustrates the differences in number of genes (presented in brackets) in each functional subsystem. These genes are very important in mediating host response to each individual bacterium. Importantly these genes, both in number and function, are different between the various strains. The results are summarised below:

*R. hominis* A2-183
Cell Wall and Capsule (57)
Membrane Transport (24)
Motility and Chemotaxis (49)
Regulation and Cell signaling (16)
Dormancy and Sporulation (12)
Carbohydrates (271)
*E. rectale* ATCC 33656
Cell Wall and Capsule (41)
Membrane Transport (13)
Motility and Chemotaxis (16)
Regulation and Cell signaling (9)
Dormancy and Sporulation (6)
Carbohydrates (172)
*R. intestinalis* L1-82
Cell Wall and Capsule (35)
Membrane Transport (36)
Motility and Chemotaxis (15)
Regulation and Cell signaling (10)
Dormancy and Sporulation (17)
*R. intestinalis* M50/1
Cell Wall and Capsule (28)
Membrane Transport (37)
Motility and Chemotaxis (17)
Regulation and Cell signaling (10)
Dormancy and Sporulation (17) Carbohydrates (201)
*R. inulinovorans* DSM 16841
Cell Wall and Capsule (69)
Membrane Transport (26)
Motility and Chemotaxis (14)
Regulation and Cell signaling (9)
Dormancy and Sporulation (17)
Carbohydrates (160)

Percentage Sequence Identity of >3000 Genes Found in Contig 1 Highlights the Differences Between the Bacterial Genome of *R. hominis* and the Bacterial of *E. rectale, R. intestinalis* and *R. inulinivorans*

Comparisons were made between the genomes of various *Roseburia* species and the related species *Eubacterium rectale*, the closest relative to *R. hominis*.

*R. hominis* reference genome 585394.12
*E. rectale* genome ATCC336556 515619.3
*R. intestinalis* L1-82166486.4
*R. intestinalis* MS0/1166486.5
*R. inulinovorans* DSM16841 622312.3

The percentage identity of potential genes between the various *Roseburia* genomes ranges from 0% to around 90% sequence identity. Many genes are hypothetical and vary between the strains. Large numbers of genes are present in the *R. hominis* genomes that are absent from the genomes of the others *Roseburia* species

*Roseburia hominis* has 924 genes that are not found in the other genomes of other *Roseburia* species (0% identity) indicting that almost 25% of its genome is unique to *R. hominis*. Also the low homology between other genes (<10-70%) indicates that the functions of many others genes are also likely to differ.

The information provides compelling evidence that these bacteria are very different from a genome and functional perspective, and cannot be grouped other than by their phylogenetic relatedness, which is generally based on the conserved gene 16S ribosomal gene which is a conserved piece of prokaryotic DNA found in all bacteria. 16S rRNA gene sequences are used for bacterial phylogeny and taxonomy studies (shared genetic marker).

Functionality in Relation to Host Response and Immunity is Bacterial Strain Specific FIG. 9 illustrates a comparison of gene expression data for three strains of bacteria from Cluster XIVa (Firmicutes), namely *Roseburia hominis, E. rectale* and *Roseburia intestinalis*. The data indicates the numbers of unique genes expressed by the phylogenetically related bacterial strains following exposure to human epithelial cells. Gene expression was determined by using Affymetrix human microarrays containing 56,000 genes. This difference reflects the differences in their respective genomes. [These experiments are similar to those described elsewhere in the specification using mouse microarrays but used specific human microarrays. The GeneChip® Human Genome 0133 Plus 2.0 Array is the first and most comprehensive whole human genome expression array. The Affymetrix GeneChip® Human Genome U133 Plus 2.0 Array (HG-U133 Plus 2.0) microarray comprises 1,300,000 unique oligonucleotide features covering over 47,000 transcripts and variants, which, in turn, represent approximately 39,000 of the best characterized human genes. The cell lines used to evaluate the signalling responses induced by different commensal bacteria include the human colon cell line Caco-2 cells and HT-29 cells and bacteria including *R. hominis, E. rectale* and *R. intestinalis* where compared against *Salmonella enteritidis*, an enteric pathogen.

Functional Differences in Cluster XIV a Bacteria—Comparison Between *R. hominis* and *E. rectale*

FIG. 10 shows that *Roseburia hominis* induces A20 a negative regulator of NF-κB signaling with potent anti-inflammatory activity whereas other bacterial strains have no effect. The flagellin moiety of *Roseburia hominis* also induces A20 unlike that of *Eubacterium rectale*, a related bacterium.

Cell culture reagents, unless specified otherwise, were supplied by Sigma-Aldrich. Caco-2 (ECACC Cat No. 8601 02002) and HT29 (ATCC) cell lines cultured in Dulbecco's Modified Eagle Medium (DMEM) supplemented with 10% Foetal Bovine Serum (FBS) (Gibco, UK), 200 mM L-glutamine and 1% antibiotics/antimycotics were seeded in six-well transwell plate (Coming). Cells were incubated at 37° C. in a 5% C02 atmosphere until 3 days post-confluence, washed with Hanks' solution to remove antibiotics and FCS and stepped down in DMEM supplemented with L-glutamine, sodium selenite and transferrin for 24 h without antibiotics. Transwell inserts were then transferred to an anaerobic culture box within the anaerobic workstation at 37° C. The upper compartment of each insert was filled with anaerobic DMEM cell medium, while the lower compartment was filled with oxygenated DMEM.

*Roseburia hominis* A2-183 and *E. rectale* ATCC336556 in standard YCFA and M2 culture media and *Salmonella enteric serovar enteritidis* cultured in LB broth were harvested at exponential phase by centrifugation at 3,500×g for 5 min. The pellet was washed and resuspended in anaerobic DMEM. One hundred microliters of bacterial suspension (108 CFU/mL) was added to experimental wells. The control wells received the same amount of medium without bacterial cells. Additional control included bacterial cells incubated without Caco-2 or HT29 cells.

Bacterial and eukaryotic cells were harvested after 2 hand 4 h incubation. Both non-adherent and adherent bacteria were aspirated and stored in RNALater. Caco-2 cells or HT-29 cells were harvested from the wells and also stored in RNALater.

Luciferase Assay for Determination of A20 Luciferase Gene Expression

Fugene® 6 transfection reagent (Roche, UK) was used for the transfection of HT29 cells with the plasmids carrying the luciferase reporter gene under the control of the A20 promoterpLuc-A20 and pLuc-A20Δ NF-KB (mutated in 3 nucleotides in the A20 promoter region) and the GFP reporter gene under the control of the A20 promoter pCA-GGS-GFP\A20 and pLuc-GL2\NF-κB. After 48 h, the cells were stimulated with live bacteria *R. hominis, E. rectale* and *S. enteritidis* and recombinant flagellins; *S. enteritidis* and *R. hominis* (Fla 1) (100 ng/ml) for 9, 12 and 24 h. Recombinat flagellin were generated using full length sequences cloned into appropriate vectors and expressed in *E. coli* JM109, BL21 and Rosetta. Luciferase (Firefly-f-Lue and renilla-r-Luc) activities were determined using the DualGlo® luciferase assay system (Promega, UK) and an Envision 2102 Multilabel Reader. The relative luciferase reporter activity was obtained by normalization to renilla control.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention, which are obvious to those skilled in the relevant fields are intended to be within the scope of the following claims.

What is claimed is:

1. A pharmaceutical composition that comprises: the bacteria species *Roseburia hominis*; and a pharmaceutically acceptable excipient, carrier or diluent;
   wherein the bacteria species is present in an amount sufficient to treat a disorder when administered to a subject in need thereof;
   wherein the bacteria strain is lyophilized; and
   wherein at least $1 \times 10^3$ colony forming units of the lyophilized bacteria are provided in one or more doses.

2. The pharmaceutical composition of claim 1, wherein the disorder is an inflammatory disorder, an immune disorder, or an intestinal disorder.

3. A method of making a pharmaceutical composition that comprises the bacteria species *Roseburia hominis*, the method comprising:
   growing a population of bacteria species *Roseburia hominis* in a culture media under anaerobic conditions comprising a mixture of $N_2$, $CO_2$ and $H_2$;
   lyophilizing the population of the bacteria species to obtain at least $1 \times 10^3$ colony forming units of lyophilized bacteria; and
   admixing the lyophilized bacteria with a pharmaceutically acceptable excipient, carrier or diluent.

4. The pharmaceutical composition according to claim 1, wherein the disorder is selected from the group consisting of irritable bowel syndrome (IBS), colitis, inflammatory bowel disorder (IBD), pouchitis, functional dyspepsia, functional constipation, functional diarrhea, antibiotic associated diarrhoea, traveler's diarrhea, pediatric diarrhea, functional abdominal pain, functional bloating, Epigastric Pain Syndrome, Postprandial Distress Syndrome, gastroesophageal reflux disease (GERD), autoimmune diseases, diabetes, arthritis, multiple sclerosis, psoriasis, allergies, coeliac disease, atopic diseases, atopic dermatitis, rhinitis, necrotising enterocolitis and combinations thereof.

5. The pharmaceutical composition of claim 1, wherein the pharmaceutical composition comprises a pharmaceutically acceptable carrier, wherein the pharmaceutically acceptable carrier is selected from the group consisting of lactose, starch, glucose, methyl cellulose, magnesium stearate, mannitol, sorbitol, and combinations thereof.

6. The pharmaceutical composition of claim 1, wherein the pharmaceutical composition comprises a pharmaceutically acceptable diluent, wherein the pharmaceutically acceptable diluent is selected from the group consisting of ethanol, glycerol, water and combinations thereof.

7. The pharmaceutical composition of claim 1, wherein the pharmaceutical composition is an edible composition.

8. The pharmaceutical composition of claim 1, wherein the pharmaceutical composition is a probiotic composition.

9. The pharmaceutical composition of claim 8, wherein the pharmaceutical composition further comprises a prebiotic compound.

10. The pharmaceutical composition of claim 9, wherein the prebiotic compound is a carbohydrate, inulin or a trans-galacto-oligosaccharide.

11. The pharmaceutical composition of claim 10, wherein the pharmaceutical composition comprises the carbohydrate, and wherein the carbohydrate is selected from the group consisting of: fructo-oligosaccharides; short-chain fructo-oligosaccharides; isomalt-oligosaccharides; pectins, xylooligosaccharides; chitosan-oligosaccharides; beta-glucans; arable gum modified and resistant starches; polydextrose; D-tagatose; acacia fibers; carob; oats; and citrus fibers.

12. The pharmaceutical composition of claim 9, wherein the prebiotic compound is in an amount of from about 1% to about 20% by weight with respect to a total weight of the composition.

13. The pharmaceutical composition of claim 1, wherein the administration is selected from the group consisting of oral, rectal, vaginal, parenteral, intramuscular, intraperitoneal, intraarterial, intrathecal, intrabronchial, subcutaneous, intradermal, intravenous, nasal, buccal, and sublingual.

14. The pharmaceutical composition of claim 1, wherein the amount of the bacteria species is from about $1\times10^6$ to about $1\times10^{11}$ colony forming units per gram with respect to a weight of the composition.

15. The pharmaceutical composition of claim 1, wherein the composition is administered at a dose of 1 g, 3 g, 5 g or 10 g.

16. The pharmaceutical composition of claim 1, wherein the pharmaceutical composition further comprises at least one additional bacterium.

17. The pharmaceutical composition of claim 16, wherein the at least one additional bacterium is a food grade bacterium.

18. The pharmaceutical composition of claim 17, wherein the food grade bacterium is selected from the group consisting of lactic acid bacteria, bifidobacteria, propionibacteria, and mixtures thereof.

19. The pharmaceutical composition of claim 1, wherein the pharmaceutical composition is in the form of a suppository, a pessary, a suspension, an emulsion, a lotion, an ointment, a cream, a gel, a spray, a solution or a dusting powder.

20. The pharmaceutical composition of claim 1, wherein the bacteria species comprises a bacteria strain that has a DNA-DNA identify of at least 70% with a strain deposited under accession number NCIMB 14029, as measured by a sequence alignment performed using BLAST.

21. The pharmaceutical composition of claim 1, wherein the bacteria species comprises a bacteria strain that has a 16S rRNA identity of at least 99.5% with the strain deposited under accession number NCIMB 14029, as measured by a sequence alignment performed using BLAST.

22. The pharmaceutical composition of claim 1, wherein the bacteria species comprises the bacteria strain deposited under accession number NCIMB 14029.

* * * * *

SEQUENCE LISTING

<160> NUMBER OF SEQ ID NOS: 4

<210> SEQ ID NO 1
<211> LENGTH: 15
<212> TYPE: PRT

```
<213> ORGANISM: Roseburia hominis

<400> SEQUENCE: 1

Ala Gln Tyr Asn Asp Asp Ala Lys Ser Val Leu Glu Ile Leu Lys
1               5                   10                  15

<210> SEQ ID NO 2
<211> LENGTH: 14
<212> TYPE: PRT
<213> ORGANISM: Roseburia hominis

<400> SEQUENCE: 2

Gly Leu Asn Lys Ala Ser Arg Asn Ser Gln Asp Gly Ile Ser
1               5                   10

<210> SEQ ID NO 3
<211> LENGTH: 18
<212> TYPE: DNA
<213> ORGANISM: Artificial Sequence
<220> FEATURE:
<223> OTHER INFORMATION: General bacterial probe Eub338

<400> SEQUENCE: 3
gctgcctccc gtaggagt                                              18

<210> SEQ ID NO 4
<211> LENGTH: 23
<212> TYPE: DNA
<213> ORGANISM: Artificial Sequence
<220> FEATURE:
<223> OTHER INFORMATION: Roseburia hominis A2-183-specific probe

<400> SEQUENCE: 4
gtacattaca tactctgtca gtg                                        23
```